(12) United States Patent
Brau et al.

(10) Patent No.: US 11,584,910 B2
(45) Date of Patent: Feb. 21, 2023

(54) SYSTEM AND METHOD FOR CELL CULTURE SCALING

(71) Applicant: LIFE TECHNOLOGIES CORPORATION, Carlsbad, CA (US)

(72) Inventors: Christopher Brau, Grand Island, NY (US); Nephi Jones, Newton, UT (US); Mark Smith, Nibley, UT (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 1054 days.

(21) Appl. No.: 16/238,591

(22) Filed: Jan. 3, 2019

(65) Prior Publication Data
US 2019/0218496 A1 Jul. 18, 2019

Related U.S. Application Data

(60) Provisional application No. 62/712,343, filed on Jul. 31, 2018, provisional application No. 62/670,934, (Continued)

(51) Int. Cl.
*B01F 23/00* (2022.01)
*B01F 27/00* (2022.01)
(Continued)

(52) U.S. Cl.
CPC ........... *C12M 35/04* (2013.01); *B01F 23/233* (2022.01); *B01F 27/054* (2022.01);
(Continued)

(58) Field of Classification Search
CPC ............ B01F 2035/352; B01F 2101/44; B01F 23/233; B01F 23/23362; B01F 27/054;
(Continued)

(56) References Cited

U.S. PATENT DOCUMENTS

| | | |
|---|---|---|
| 659,345 A | 10/1900 | Ivins |
| 1,711,114 A | 4/1929 | Hunt |

(Continued)

FOREIGN PATENT DOCUMENTS

| | | |
|---|---|---|
| CN | 101163538 A | 4/2008 |
| CN | 202606066 U | 12/2012 |

(Continued)

OTHER PUBLICATIONS

Stoker, Emily B., "Comparative Studies on Scale-Up Methods of Single-Use Bioreactors" (2011). All Graduate Theses and Dissertations. 889. (Year: 2011).*

(Continued)

*Primary Examiner* — Anshu Bhatia
(74) *Attorney, Agent, or Firm* — Mintz, Levin, Cohn, Ferris, Glovsky and Popeo, P.C.

(57) ABSTRACT

The present set of embodiments relate to a bioproduction system, method, and apparatus for creating a scalable bioreactor system. Specifically, the present set of embodiments enable the determination of bioreaction performance characteristics of a commercial scale by matching operational parameters between a small test scale bioreaction to that of a commercial scale bioreaction. The system and methods do not rely on simply making bioreactor apparatuses across scales the same dimensionally which would not account for differences in fluid dynamic properties between very small to very large volumes, but requires tuning of a variety of systems (mixing assembly, sparger system, and headspace airflow system) in conjunction with one another to achieve predictive outcomes.

17 Claims, 30 Drawing Sheets

Related U.S. Application Data filed on May 14, 2018, provisional application No. 62/618,215, filed on Jan. 17, 2018.

(51) Int. Cl.

| | | |
|---|---|---|
| *C12M 1/42* | (2006.01) | |
| *C12M 1/00* | (2006.01) | |
| *C12N 5/071* | (2010.01) | |
| *C12M 1/06* | (2006.01) | |
| *B01F 23/233* | (2022.01) | |
| *B01F 27/054* | (2022.01) | |
| *B01F 27/92* | (2022.01) | |
| *B01F 27/114* | (2022.01) | |
| *B01F 27/213* | (2022.01) | |
| *B01F 35/43* | (2022.01) | |
| *B01F 35/513* | (2022.01) | |
| *B01F 35/32* | (2022.01) | |
| *B01F 35/41* | (2022.01) | |
| *C12M 1/36* | (2006.01) | |
| *B01F 27/90* | (2022.01) | |
| *B01F 35/30* | (2022.01) | |
| *B01F 101/44* | (2022.01) | |

(52) U.S. Cl.
CPC .......... *B01F 27/114* (2022.01); *B01F 27/213* (2022.01); *B01F 27/92* (2022.01); *B01F 35/3204* (2022.01); *B01F 35/4121* (2022.01); *B01F 35/43* (2022.01); *B01F 35/513* (2022.01); *C12M 23/50* (2013.01); *C12M 23/58* (2013.01); *C12M 27/02* (2013.01); *C12M 27/06* (2013.01); *C12M 41/48* (2013.01); *C12N 5/0602* (2013.01); *B01F 23/23362* (2022.01); *B01F 27/90* (2022.01); *B01F 35/3214* (2022.01); *B01F 2035/352* (2022.01); *B01F 2101/44* (2022.01); *C12N 2527/00* (2013.01)

(58) Field of Classification Search
CPC ...... B01F 27/114; B01F 27/213; B01F 27/90; B01F 27/92; B01F 35/3204; B01F 35/3214; B01F 35/4121; B01F 35/43; B01F 35/513; C12M 23/50; C12M 23/58; C12M 27/02; C12M 27/06; C12M 35/04; C12M 41/48; C12N 2527/00; C12N 5/0602
USPC ............ 435/394, 289.1, 296.1, 302.1, 303.1
See application file for complete search history.

(56) References Cited

U.S. PATENT DOCUMENTS

| | | |
|---|---|---|
| 1,752,833 A | 4/1930 | Brumder |
| 1,778,188 A | 10/1930 | Guy |
| 1,898,724 A | 2/1933 | Gifford |
| 1,954,093 A | 4/1934 | Nelson |
| 2,552,057 A | 5/1951 | Paik |
| 2,896,926 A | 7/1959 | Chapman |
| 3,281,124 A | 10/1966 | Bartl |
| 3,322,401 A | 5/1967 | Mersch |
| 3,559,962 A | 2/1971 | Enssle et al. |
| 3,692,427 A | 9/1972 | Risse |
| 4,083,653 A | 4/1978 | Stiffler |
| 4,355,906 A | 10/1982 | Ono |
| D273,709 S | 5/1984 | Schneider |
| 4,712,922 A | 12/1987 | Feterl |
| 4,722,608 A | 2/1988 | Salzman et al. |
| D336,034 S | 6/1993 | Rebilas |
| 5,411,331 A | 5/1995 | Griffin |
| 5,454,797 A | 10/1995 | Haswell |
| D373,709 S | 7/1996 | Leu |
| 5,885,001 A | 3/1999 | Thomas |
| 5,896,989 A | 4/1999 | Ropiak et al. |
| 5,941,636 A | 8/1999 | Lu |
| 6,083,587 A | 7/2000 | Smith et al. |
| D439,328 S | 3/2001 | Nielsen |
| 6,655,655 B1 | 12/2003 | Matkovich et al. |
| 6,670,171 B2 | 12/2003 | Carll |
| 6,844,186 B2 | 1/2005 | Carll |
| 6,884,786 B1 | 4/2005 | Fluckiger et al. |
| 7,229,206 B2 | 6/2007 | Whitney |
| 7,384,783 B2 | 6/2008 | Kunas et al. |
| 7,441,940 B2 | 10/2008 | Vanek |
| 7,487,688 B2 | 2/2009 | Goodwin |
| 7,682,067 B2 | 3/2010 | West et al. |
| 7,878,099 B2 | 2/2011 | Loibl |
| 7,879,599 B2 | 2/2011 | Goodwin et al. |
| D662,212 S | 6/2012 | Quisenberry |
| 8,272,410 B2 | 9/2012 | Elgan et al. |
| 8,342,737 B2 | 1/2013 | Greller et al. |
| 8,348,737 B2 | 1/2013 | Everett |
| D679,023 S | 3/2013 | Quisenberry |
| 8,455,242 B2 | 6/2013 | Staheli et al. |
| 8,506,198 B2 | 8/2013 | West et al. |
| 8,603,805 B2 | 12/2013 | Goodwin et al. |
| 8,641,314 B2 | 2/2014 | Thacker et al. |
| 9,005,971 B2 | 4/2015 | Jones et al. |
| 9,388,375 B2 | 7/2016 | Brau et al. |
| 9,643,133 B2 | 5/2017 | Goodwin et al. |
| 9,839,886 B2 | 12/2017 | Staheli |
| 9,932,553 B2 | 4/2018 | Jones et al. |
| D824,042 S | 7/2018 | Scott et al. |
| D830,544 S | 10/2018 | Kisner et al. |
| D857,188 S | 8/2019 | Moran et al. |
| D870,315 S | 12/2019 | Wahlqvist et al. |
| D870,989 S | 12/2019 | Penland |
| 2002/0105856 A1 | 8/2002 | Terentiev |
| 2002/0131654 A1 | 9/2002 | Smith et al. |
| 2003/0077466 A1 | 3/2003 | Smith et al. |
| 2006/0196501 A1 | 9/2006 | Bibbo et al. |
| 2006/0240546 A1 | 10/2006 | Goodwin et al. |
| 2006/0270036 A1 | 11/2006 | Goodwin et al. |
| 2007/0014187 A1 | 1/2007 | Kaas |
| 2008/0032389 A1 | 2/2008 | Selker et al. |
| 2010/0165785 A1 | 7/2010 | Kaas |
| 2010/0260010 A1 | 10/2010 | Jornitz |
| 2011/0013473 A1 | 1/2011 | Ludwig et al. |
| 2011/0013474 A1 | 1/2011 | Ludwig et al. |
| 2011/0026360 A1 | 2/2011 | Greller et al. |
| 2011/0058447 A1 | 3/2011 | Reif et al. |
| 2011/0058448 A1 | 3/2011 | Reif et al. |
| 2011/0188928 A1 | 8/2011 | West et al. |
| 2011/0207218 A1 | 8/2011 | Staheli et al. |
| 2011/0229963 A1 | 9/2011 | Fatherazi et al. |
| 2011/0310696 A1 | 12/2011 | Goodwin et al. |
| 2011/0312087 A1* | 12/2011 | Khan .................. C12M 29/06 435/325 |
| 2013/0082410 A1 | 4/2013 | Goodwin et al. |
| 2013/0101982 A1 | 4/2013 | Goodwin et al. |
| 2013/0279289 A1 | 10/2013 | Eggler et al. |
| 2013/0288346 A1* | 10/2013 | Tuohey .................. C12M 27/02 435/287.1 |
| 2014/0106453 A1 | 4/2014 | Kunas et al. |
| 2015/0117142 A1 | 4/2015 | Staheli et al. |
| 2015/0118753 A1* | 4/2015 | Brau .................... B01F 23/233 366/101 |
| 2017/0011714 A1 | 1/2017 | Eim et al. |
| 2017/0183617 A1 | 6/2017 | Jones et al. |

FOREIGN PATENT DOCUMENTS

| | | |
|---|---|---|
| DE | 202009005407 U1 | 9/2009 |
| DE | 102008058338 A1 | 5/2010 |
| EP | 1776998 A1 | 4/2007 |
| EP | 2123745 A2 | 11/2009 |
| FR | 782935 | 9/1934 |
| JP | H06285353 A | 10/1994 |
| JP | 2004-532719 A | 10/2004 |
| JP | 2013-544186 A | 12/2013 |
| WO | 2010/089151 A1 | 8/2010 |

(56) References Cited

FOREIGN PATENT DOCUMENTS

| WO | 2011/139209 A1 | 11/2011 |
| WO | 2012/097079 A2 | 7/2012 |
| WO | 2013/151733 A1 | 10/2013 |
| WO | 2015/039034 A1 | 3/2015 |
| WO | 2017/023638 A1 | 2/2017 |
| WO | 2017/064058 A1 | 4/2017 |

OTHER PUBLICATIONS

Yang, J.-D et al. (2007). Fed-batch bioreactor process scale-up from 3-L to 2,500-L scale for monoclonal antibody production from cell culture. In Biotechnology and Bioengineering (vol. 98, Issue 1, pp. 141-154). Wiley. (Year: 2007).*

De Wilde, Davy, et al. "Superior scalability of single-use bioreactors." Innovations in Cell Culture 14 (2014): 14-19. (Year: 2014).*

Xing, Z., et al.. (2009). Scale-up analysis for a CHO cell culture process in large-scale bioreactors. In Biotechnology and Bioengineering (vol. 103, Issue 4, pp. 733-746). Wiley. (Year: 2009).*

International Search Report and Written Opinion dated Apr. 20, 2017, issued in PCT Application No. PCT/US2016/068064, filed Dec. 21, 2016.

Communication under Rule 71(3) EPC received for European Application No. 16826262.4, dated Sep. 24, 2021, 6 pages.

ATMI Life Sciences, *Integrity PadReadtor, A New Culture in Cell Growth*, published as early as 2010, 4 pages.

ATMI Life Sciences, *Integrity PadReadtor, All Applications, High-End Controls and Abilities*, published as early as 2010, 4 pages.

\* cited by examiner

FIG. 23 — Table 2300

Thermo Fisher SUB Vessel Platform

| | 50 | 1 no. imp. | 100 | 1 no. imp. | 250 | 1 no. imp. | 500 | 2 no. imp. | 1000 | 3 no. imp. | 2000 | 3 no. imp. |
|---|---|---|---|---|---|---|---|---|---|---|---|---|
| Rated working volume (liters) | 50 | | 100 | | 250 | | 500 | | 1000 | | 2000 | |
| Vessel diameter (cm) | 34.93 | 34.93 | 43.82 | 43.82 | 59.69 | 59.69 | 75.57 | 75.57 | 95.89 | 95.89 | 119.38 | 119.38 |
| Vessel/impeller diameter | 2.97 | 2.97 | 3.00 | 2.62 | 2.98 | 3.19 | 3.01 | 2.86 | 2.99 | 3.14 | 3.00 | 2.77 |
| Standard Impeller Diameter (in) | 4.63 | 4.63 adj. imp. | 5.75 | 6.58 adj. imp. | 7.88 | 7.36 adj. imp. | 9.88 | 10.40 adj. imp. | 12.63 | 12.02 adj. imp. | 15.67 | 16.97 adj. imp. |
| Rted working volume (liters) | 11.75 | 11.75 adj. imp. | 14.61 | 16.71 adj. imp. | 20.00 | 18.68 adj. imp. | 25.08 | 26.42 adj. imp. | 32.07 | 30.54 adj. imp. | 39.80 | 43.11 adj. imp. |

Target RPM at the listed Power per Volume Desired

| Power per volume in W/m^3 | 50 std | 50 adj | | 100 std | 100 adj | | 250 std | 250 adj | | 500 std | 500 adj | | 1000 std | 1000 adj | | 2000 std | 2000 adj | | Power per volume in HP/1kgal |
|---|---|---|---|---|---|---|---|---|---|---|---|---|---|---|---|---|---|---|---|
| 1 | 67.23 | 67.23 | 0.41 | 58.92 | 47.09 | 0.41 | 47.35 | 42.11 | 0.41 | 40.91 | 29.77 | 0.41 | 34.23 | 25.74 | 0.41 | 30.08 | 18.26 | 0.41 | 0.01 |
| 5 | 114.96 | 114.96 | 0.71 | 100.76 | 80.53 | 0.70 | 80.96 | 72.00 | 0.70 | 69.96 | 50.91 | 0.70 | 58.53 | 44.02 | 0.70 | 51.44 | 31.23 | 0.70 | 0.03 |
| 10 | 144.84 | 144.84 | 0.89 | 126.95 | 101.46 | 0.89 | 102.01 | 90.72 | 0.89 | 88.14 | 64.15 | 0.89 | 73.74 | 55.46 | 0.89 | 64.81 | 39.34 | 0.89 | 0.05 |
| 15 | 165.80 | 165.80 | 1.02 | 145.32 | 116.14 | 1.02 | 116.77 | 103.85 | 1.02 | 100.89 | 73.43 | 1.02 | 84.41 | 63.48 | 1.02 | 74.19 | 45.04 | 1.02 | 0.08 |
| 20 | 182.48 | 182.48 | 1.12 | 159.94 | 127.83 | 1.12 | 128.52 | 114.30 | 1.12 | 111.05 | 80.82 | 1.12 | 92.90 | 69.87 | 1.12 | 81.65 | 49.57 | 1.12 | 0.10 |
| 25 | 196.57 | 196.57 | 1.21 | 172.29 | 137.70 | 1.20 | 138.45 | 123.13 | 1.20 | 119.62 | 87.06 | 1.20 | 100.08 | 75.27 | 1.20 | 87.96 | 53.40 | 1.21 | 0.13 |
| 30 | 208.89 | 208.89 | 1.28 | 183.09 | 146.33 | 1.28 | 147.12 | 130.84 | 1.28 | 127.12 | 92.52 | 1.28 | 106.35 | 79.99 | 1.28 | 93.47 | 56.74 | 1.28 | 0.15 |
| 35 | 219.90 | 219.90 | 1.35 | 192.74 | 154.04 | 1.35 | 154.88 | 137.74 | 1.35 | 133.82 | 97.40 | 1.35 | 111.95 | 84.20 | 1.35 | 98.40 | 59.73 | 1.35 | 0.18 |
| 40 | 229.91 | 229.91 | 1.41 | 201.52 | 161.06 | 1.41 | 161.93 | 144.01 | 1.41 | 139.91 | 101.83 | 1.41 | 117.05 | 88.03 | 1.41 | 102.88 | 62.45 | 1.41 | 0.20 |
| 45 | 239.12 | 239.12 | 1.47 | 209.59 | 167.50 | 1.47 | 168.41 | 149.78 | 1.47 | 145.51 | 105.91 | 1.47 | 121.74 | 91.56 | 1.47 | 107.00 | 64.95 | 1.47 | 0.23 |
| 50 | 247.67 | 247.67 | 1.52 | 217.08 | 173.49 | 1.52 | 174.43 | 155.13 | 1.52 | 150.72 | 109.69 | 1.52 | 126.09 | 94.83 | 1.52 | 110.82 | 67.27 | 1.52 | 0.25 |
| 55 | 255.66 | 255.66 | 1.57 | 224.09 | 179.09 | 1.57 | 180.06 | 160.14 | 1.57 | 155.58 | 113.23 | 1.57 | 130.16 | 97.89 | 1.57 | 114.40 | 69.45 | 1.57 | 0.28 |
| 60 | 263.18 | 263.18 | 1.62 | 230.68 | 184.36 | 1.61 | 185.36 | 164.85 | 1.61 | 160.16 | 116.57 | 1.61 | 133.99 | 100.77 | 1.61 | 117.77 | 71.49 | 1.61 | 0.30 |
| 65 | 270.30 | 270.30 | 1.66 | 236.92 | 189.35 | 1.66 | 190.37 | 169.31 | 1.66 | 164.49 | 119.72 | 1.66 | 137.61 | 103.50 | 1.66 | 120.95 | 73.42 | 1.66 | 0.33 |
| 70 | 277.06 | 277.06 | 1.70 | 242.84 | 194.08 | 1.70 | 195.13 | 173.54 | 1.70 | 168.60 | 122.71 | 1.70 | 141.05 | 106.09 | 1.70 | 123.97 | 75.26 | 1.70 | 0.35 |
| 75 | 283.51 | 283.51 | 1.74 | 248.49 | 198.60 | 1.74 | 199.67 | 177.58 | 1.74 | 172.53 | 125.57 | 1.74 | 144.34 | 108.56 | 1.74 | 126.86 | 77.01 | 1.74 | 0.38 |
| 80 | 289.67 | 289.67 | 1.78 | 253.90 | 202.92 | 1.78 | 204.02 | 181.44 | 1.78 | 176.28 | 128.30 | 1.78 | 147.47 | 110.92 | 1.78 | 129.62 | 78.68 | 1.78 | 0.41 |
| 85 | 295.58 | 295.58 | 1.82 | 259.08 | 207.06 | 1.81 | 208.18 | 185.14 | 1.81 | 179.88 | 130.92 | 1.81 | 150.48 | 113.18 | 1.81 | 132.26 | 80.29 | 1.81 | 0.43 |
| 90 | 301.27 | 301.27 | 1.85 | 264.06 | 211.04 | 1.85 | 212.19 | 188.71 | 1.85 | 183.34 | 133.43 | 1.85 | 153.38 | 115.36 | 1.84 | 134.81 | 81.84 | 1.85 | 0.46 |
| 95 | 306.75 | 306.75 | 1.89 | 268.86 | 214.88 | 1.88 | 216.04 | 192.14 | 1.88 | 186.67 | 135.86 | 1.88 | 156.17 | 117.46 | 1.88 | 137.26 | 83.32 | 1.88 | 0.48 |
| 100 | 312.04 | 312.04 | 1.92 | 273.50 | 218.59 | 1.91 | 219.77 | 195.45 | 1.91 | 189.89 | 138.20 | 1.91 | 158.86 | 119.48 | 1.91 | 139.63 | 84.76 | 1.91 | 0.51 |

SYSTEM AND METHOD FOR CELL CULTURE SCALING

CROSS-REFERENCE TO RELATED APPLICATIONS

This application claims priority to U.S. Provisional Application No. 62/712,343, filed Jul. 31, 2018, U.S. Provisional Application No. 62/670,934, filed May 14, 2018, and U.S. Provisional Application No. 62/618,215, filed on Jan. 17, 2018, which are both incorporated herein by specific reference.

BACKGROUND

The biopharmaceutical industry uses a broad range of mixing systems for a variety of processes such as in the preparation of media and buffers and in the growing, mixing and suspension of cells and microorganisms. Some conventional mixing systems, including bioreactors and fermenters, comprise a flexible bag disposed within a rigid support housing. An impeller is disposed within the flexible bag and is coupled with the drive shaft. Rotation of the drive shaft and impeller facilitates mixing and/or suspension of the fluid contained within flexible bag.

Scientist and engineers have worked to create stirred tank reactors that can provide not only an aseptic and well controlled environment for cell culture growth, but also deliver a robust scale-up solution from research to manufacturing scale. Traditionally good engineering principles have been applied in such a manner to design reactors based upon linear geometric scaling approach (i.e. the vessels will have similar height/diameter ratios as well as similar impeller/tank diameter ratios). This works fairly well in many cases, but the operators usually have to make many complex decision as how best to choose operational settings in order to have reproducible results through scale-up. Because it is a two phase and metabolically based system, most of the operational parameters interact dynamically and are often non-linear in response; the best parameter choices and process outcome are often far too unpredictable, costly, and time consuming to be addressed properly at the operator level.

Those skilled in the art of biopharma manufacturing recognize the importance of having a good scale-up and scale-down models that are able to simulate or ideally replicate the physiological growth conditions found in large-scale bioreactor. The reason for the scale-down model's importance is often related to the need to screen multiple parameters quickly (optimization of cell clone, media, critical operating parameters, or product quality) and it is beneficial to be able to perform a wide range of experiments under well controlled conditions at lower cost and with less labor. A good scale-down model will also de-risk a desired process in that there will be much less likelihood of experiencing problems at large scale that were not previously identified at small scale.

Because the large bioreactors are two phase systems (gas and liquid based) they are difficult to scale-down in a predictable manner largely due to the solubility differences of gas types and because the fluid mechanics and/or physics of the system are very dynamic (non-linear) due viscosity, shear, density, and surface interactions that are influenced across scale. While bulk power dissipation rates may be similar using traditional bioreactor designs, the resulting bulk flow and measured mixing times are rarely similar across all scales. As a result, problem often arise at large scale that have not been seen as problematic in the small scale system because the same gradients of pH, nutrients, gas concentration, or shear found at large scale are not easily replicated under a single operating state created in a small scale bioreactor.

The main design methods currently employed are geometric ratio scaling of the system (tank height to diameter ratio and an impeller to diameter ratio); this being operated in combination with either 1) near constant impeller tip speed or 2) near constant P/V (power input to volume). These approaches have been reasonably successful because it allows operators to compensate for some of the non-linearity of kinetics and mass transfer in a rotating agitator based system while being gassed. Whereas shear is traditionally benchmarked based upon tip speed of the impeller (where tip speed is a function of the square of impeller diameter). Power input to volume is more often employed because is favorable to meeting the limits of practical mechanical designs scale-up (meaning the power requirements are within reasonable magnitude across scales) because power transfer is nonlinear function of speed and diameter (and partially impeller geometry).

Once the general design of the reactor is known, common practice is to focus on one of two critical process parameters. Choose a tier 1 target constant—shear sensitive cultures often use impeller tip speed, whereas more shear tolerant cultures often use power input to volume (P/V). Mixing efficiency is important regardless of the chose scale parameter, best practice is to verify that similar or at least reasonable blend times are achievable across scales (T90 mixing times of <30 sec are most desirable, but often not achievable across scale because of bulk fluid mixing dissipation issues inherent to water based fluid). Then the second tier target is often tied to pH control and dissolved gases—mass transfer kLa of oxygen (primary) and kLa of carbon dioxide (secondary). Some systems are further optimized by use of computational fluid dynamic (CFD). This is a good method for determining impeller power number (Np) and for modeling the fluid flow profile in the system. Power transfer can be estimated and used to predict the amount of (mixing) power transferred into the system. Computational or hybrid models (RPT) can also predict fluid field direction, velocity, and localized shear conditions.

Well informed operators are often very successful in achieving acceptable outcomes if the system is designed properly, but the overall process is still often burdened with unknowns and time consuming troubleshooting especially when process transfer must be facilitated between dissimilar system as part of scale-up or transfer to an alternate location.

The issue that is often overlooked is the bulk fluid flow of the system and how this changes across scale. Fluid is displacement and velocity is not linear across scales, therefore the mixing profile of liquid movement will change not only based upon volume, tip speed, and diameter. It also depends upon the spatial distribution of power within the reactor. In practical terms, designs should detune the localized mixing performance of the smaller volume system to match the bulk mixing and mass transfer performance of the large scale system. A good design will take in the account the effects of baffling or flow disrupters in the design as some randomness in the mixing or vessel turn-over is beneficial.

SUMMARY OF INVENTION

In one aspect, a scalable bioreactor system for transitioning from testing to commercial production is disclosed. The system may include a first bioreactor comprising a first bioprocessing container having a first end, a second end, and a sidewall and a first configurable mixing assembly suspended between the first and second ends of the first bioprocessing container and a first impeller having a first diameter, the first impeller attached to the first configurable mixing assembly in a first position, wherein the first diameter and the first position are selected to achieve a set of operational parameters as well as a second bioreactor comprising a second bioprocessing container having a first end, a second end, and a sidewall, wherein the second bioprocessing container is not the same volume as the first bioprocessing container and a second configurable mixing assembly suspended between the first and second ends of the second bioprocessing container and a second impeller having a second diameter that is not the same as the first diameter, the second impeller attached to the second configurable mixing assembly in a second position, wherein the second diameter and the second position are selected to match the set of operational parameters and the operational parameters include power per volume and impeller tip speed. In some embodiments, the first bioprocessing container includes a first sparger affixed to the first end of the first bioprocessing container and having a first number of pores and each pore has a first diameter and the second bioprocessing container includes a second sparger affixed to the first end of the second bioprocessing container and having a second number of pores and each pore has a second diameter. In some embodiments, the first number of pores is not the same as the second number of pores, the first diameter is not the same as the second diameter, and the number of pores and pores sizes are selected so that the first and second bioreactors attain the same kLa. In some embodiments, the first and second locations are selected to re-entrain gas bubbles rising out of the first and second spargers. In some embodiments, the first bioreactor includes a first headspace airflow device and the second bioreactor includes a second headspace airflow device and each crossflow spargers operates to provide different rates of airflow across a headspace to match CO2 removal rates of the liquid phase to within five percent between the first and second bioreactors. In some embodiments, the second bioreactor includes a third impeller having a third diameter that is not the same as the first diameter, wherein the third impeller is attached to the second configurable mixing assembly and the third diameter and third attachment location are selected in combination with the second diameter and the second position to match the set of operational parameters. In some embodiments, the ratio of the first impeller diameter to the first bioprocessing container width is not the same as the ratio of the second impeller diameter to the second bioprocessing container width. In some embodiments, the set of operational parameters further includes bulk fluid flow and T95 mixing times. In some embodiments, the set of operational parameters is selected based on the optimal growth conditions for a cell. In some embodiments, the cell is eukaryotic and sensitive to a shear force that increases as the impeller tip speed increases. In some embodiments, the first bioprocessing container is a bench scale volume between 0.1 liters and 50 liters and the second bioprocessing container is a commercial volume between 50 liters and 10,000 liters. In some embodiments, the first and second bioprocessing containers are rectangular in shape and the first and second configurable mixing assemblies are offset from a center axis to increase bulk fluid flow. In some embodiments, the aspect ratio of the first and second bioprocessing containers is greater than 1.5. In some embodiments, the first bioprocessing container has an aspect ratio between 1.5 and 2 and the second bioprocessing container has an aspect ratio between 1.75 and 4.

In one aspect, a method of matching fluid mixing characteristics between bioreactors having different volumes is disclosed. The method may include selecting a first bioreactor having a set of operational parameters, the first bioreactor comprising: a first bioprocessing container having a first end, a second end, and a sidewall; and a first configurable mixing assembly suspended between the first and seconds ends of the first bioprocessing container The method may include selecting a first impeller having a first diameter and attaching the first impeller to the configurable mixing assembly, wherein the first diameter and the attachment location are selected to conform to the operational parameters. The method may include selecting a second bioreactor, comprising: a second bioprocessing container having a first end, a second end, and a sidewall, wherein the second bioprocessing container is not the same volume as the first bioprocessing container; and a second configurable mixing assembly suspended between the first and second ends of the second bioprocessing container. The method may include selecting a second impeller having a second diameter that is not the same as the first diameter and attaching the second impeller to the second configurable mixing assembly, wherein the second diameter and the second attachment location are selected to match the set of operational parameters, wherein the set of operational parameters include power per volume and impeller tip speed. The method may include the step of selecting a third impeller having the third diameter that is not the same as the first diameter and attaching the third impeller to the second configurable mixing assembly, wherein the third diameter and the third attachment location are selected in combination with the second diameter and the second attachment location to match the set of operational parameters. In some embodiments, the step of adding the third impeller reduces the required second and third impeller tip speeds to maintain a power per volume and impeller tip speed in the first and second bioreactors. In some embodiments, the ratio of the first impeller diameter to the first bioprocessing container width is not the same as the ratio of the second impeller diameter to the second bioprocessing container width. In some embodiments, the set of operational parameters further includes bulk fluid flow and T95 mixing times. In some embodiments, the set of operational parameters is selected based on optimal growth conditions for a cell. In some embodiments, the cell is eukaryotic and sensitive to a shear that increases as the impeller tip speed increases. In some embodiments, the first bioprocessing container is a bench scale volume between 0.1 liters and 50 liters and the second bioprocessing container is a commercial volume between 50 liters and 10,000 liters. In some embodiments, the first and second bioprocessing containers are rectangular in shape and the first and second configurable mixing assemblies are offset from a center axis to increase bulk fluid flow. In some embodiments, the aspect ratio of the first and second bioprocessing containers is greater than 1.5.

In one aspect, a method of matching fluid mixing characteristics between bioreactors having different volumes is disclosed. The method may include selecting a first bioreactor having an operational parameter, the first bioreactor comprising a first bioprocessing container having a first end, a second end, and a sidewall and a first configurable mixing assembly suspended between the first and seconds ends of the first bioprocessing container. The method may include the step of selecting a first sparger having a first number of pores, wherein the pores have a first diameter, wherein in the first number and first diameter are selected to conform to the operational parameter, wherein the first sparger is affixed to the first end. The method may include the step of selecting a second bioreactor, comprising a second bioprocessing container having a first end, a second end, and a sidewall, wherein the aspect ratio of the second bioprocessing container is not the same as the aspect ratio of the first bioprocessing container and a second configurable mixing assembly suspended between the first and second ends of the second bioprocessing container. The method may include the step of selecting a second sparger having a second number of pores, wherein the pores have a second diameter and the second sparger is affixed to the first end of the second bioprocessing container, wherein the second number of pores and first number of pores are not the same and the second diameter and first diameter are not the same, wherein the second number of pores and second diameter are selected to match the operational parameter to within five percent, wherein the operational parameter is kLa. In some embodiments, the first bioreactor includes a first headspace airflow device and the second bioreactor includes a second headspace airflow device and each headspace airflow device operates to provide different rates of airflow across a headspace to match the operational parameter. The method may include the step attaching a second impeller to the second mixing assembly, wherein the second impeller is configured to re-entrain gas bubbles rising out of the second sparger, wherein the location of the sparger and second impeller in combination with the second number and second pore size are selected to match the operational parameter. In some embodiments, the aspect ratio of the first bioprocessing container is between 1.5 and 2 and the aspect ratio of the second bioprocessing container is between 1.75 and 4. In some embodiments, the first bioprocessing container is a bench volume between 0.1 liters and 50 liters and the second bioprocessing container is a commercial volume between 50 liters and 10,000 liters. In some embodiments, the first and second bioprocessing containers are rectangular in shape and the first and second mixing assemblies are offset from a center axis to achieve a desired kLa.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

FIG. 23 illustrates a matching operational parameters chart 2300 in accordance with one embodiment.

DETAILED DESCRIPTION

Description

Figure 1:
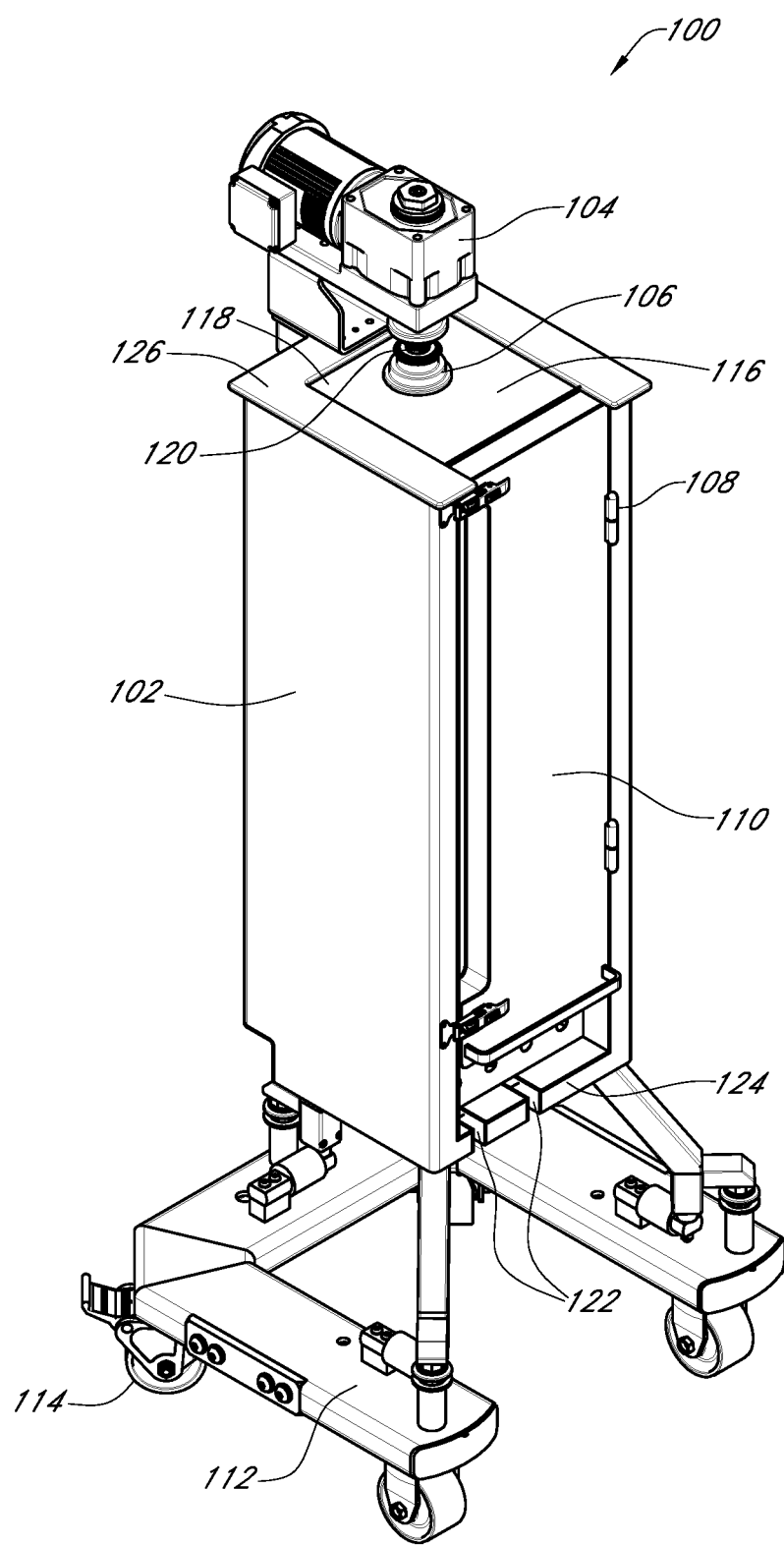
FIG. 1 illustrates a mixing system 100 in accordance with one embodiment.

Embodiments of systems, methods, and apparatuses for bioreactor scaling are described in the accompanying description and figures. In the figures, numerous specific details are set forth to provide a thorough understanding of certain embodiments. A skilled artisan will be able to appreciate that the scalable bioreactor systems and methods described herein may be used for a variety of applications including, but not limited to, bringing a cell culture product from laboratory or bench scale to commercial scale production. Additionally, the skilled artisan will appreciate that certain embodiments may be practiced without these specific details. Furthermore, one skilled in the art will readily appreciate that the specific sequences in which methods are presented and performed are illustrative and it is contemplated that the sequences may be varied and still remain within the spirit and scope of certain embodiments.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Furthermore, in described various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art will readily appreciate that the sequence may be varied and still remain within the spirit and scope of the various embodiments.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention described herein is a scalable bioreactor system and set of methods that enables manufacturers in the bioproduction space to predict the physiological growth conditions previous discussed by altering the hardware between scales to achieve similar mixing profiles and growth conditions between the two or more scales. For example, a scaled bioreactor system may include two or more different sized bioreactors that achieve similar bulk fluid, similar shear forces at the impeller tip, and similar power input per volume ratios by altering the geometry of the tanks, size and number of impellers, impeller to tank diameter (width) ratios, sparge designs, and CO2 blanket removal systems between the two or more scales. Stated differently, the two or more bioreactors in the present invention can have vastly different physical characteristics while still achieving similar mixing profiles and growth conditions in order to make predictions for commercial scale bioproduction systems at small scales, including, benchtop scales.

The magnitude of localized shear, mixing power dissipation rate, and bulk fluid flow should all be more fully addressed in scale-up design. This can be done by optimizing the power distribution of impellers (increasing the quantity of impeller in larger vessels). By putting a limit of how far impeller are spaced (increasing quantity as volume increases) or optimizing bulk fluid mixing properties using CFD or RPT models and also altering the size or shape of the impellers (not necessary the shape but either the swept area, blade geometry, surface texture properties, or diameter in order to match hydrodynamic (eddy) profiles created by fluid movement of the agitator). The primary goal is to achieve nearly identical maximum shear levels across at least 3 magnitudes of volume scale while delivering similar P/V, bulk flow, T95 mixing times, and doing so with a reasonable power input values for cell culture and within practical limits imposed by cell culture sensitivity that can occur in very large working volumes (>1000 L). The invention described herein will enable reactor scale-up to be more predictable across scale and thus more easily/logically tuned because the shear distribution is similar and the bulk fluid movement is nearly identical. The objective of the current invention is to address the unmet need that now exists due to a wide breadth of cell culture process sensitivity variances that are inherent impacted when altering cell lines, fluid type, cell density, or media formulations.

The methods herein, are designed to achieve the desired outcome of designing and characterizing reactor scale-up will be more predictable across scale and thus more easily/logically tuned because the shear distribution is more similar and the bulk fluid movement is nearly identical. The objective here is to address the unmet need that now exists due to a wide breadth of cell culture process sensitivity variances that are inherent impacted when altering cell lines, fluid type, cell density, or media formulations.

In regards to non-circular vessels, using rectangular vessels with a center drive agitator that is off set from center line is beneficial for many reasons. The unbalanced design of these two geometries (non-square and non-centered) may create improved baffling effects and desirable mixing turn over (bulk flow) within the system. Our data supports the idea that mass transfer and mixing performance is improved through our performance measurement are showing >2× improvement in kLa and mixing compared to circular designs at similar working volumes. The scaling of the impeller to match tip speed and P/V will result in a proportionally smaller impeller as the vessel rated working volumes decreases. This helps to compensate for the inherent changes in fluid mechanics that occur at smaller scale (proportionally larger impeller to vessel wall clearance will encourage and induce bulk flow much more representative to that of large scale systems). These mixing design features are then combined with optimal sparge position and this will be responsible for dramatically increasing bioreactor efficiency at large scale. Two phase mixing efficiency gains will increase bubble residence time within the liquid column and overall improved bubble distribution from the multiple impellers are both highly desirable attributes that are known to significantly improve mass transfer performance.

FIG. 1 illustrates a fluid mixing system 100 according to various embodiments. The mixing system 100 generally comprises a rigid housing 102, a motor 104 mounted to the rigid housing 102, a first bearing assembly 106 in rotational communication with the motor 104 through a drive shaft 120 and providing rotational movement to the interior of a flexible compartment 118, a hinges 108 to secure a door 110 to the rigid housing 102 and provide enclosure for the flexible compartment 118, a rigid housing support 112 for the rigid housing 102 to mount thereto, and a support wheels 114 affixed to the rigid housing support 112 and provide mobility to the mixing. The rigid housing 102 may have rigid housing openings 122 cut into rigid housing floor 124 for retaining one port 228 or more and a second bearing assembly 222 from the flexible compartment 218. In some embodiments, the rigid housing may be fixed in place and not require support wheels 114. In such embodiments, the rigid housing support 112 may be bolted to the bolt or simply held in place by the weight of the rigid housing 102.

Figure 2:
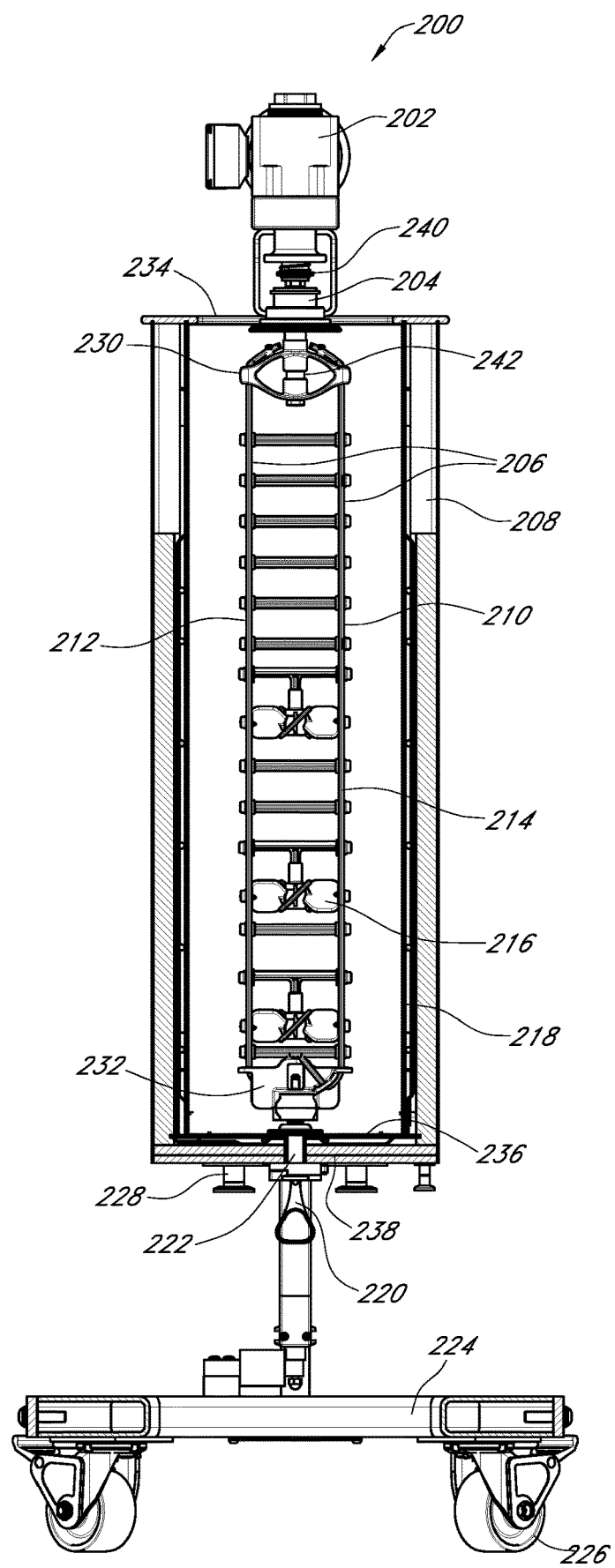
FIG. 2 illustrates a mixing system 200 in accordance with one embodiment.

FIG. 2 illustrates a cross sectional view of a fluid mixing system 200 according to various embodiments. The mixing system 200 comprises a motor 202 mounted to a rigid housing 208 having a drive shaft 120 that is in sterile, rotational communication to the interior of a flexible compartment 218 through a first bearing assembly 204. The mixing system 200 also comprises a helical assembly 214 comprised of a yoke 230 and a yoke/impeller 232 that act to suspend a driveline 206 between a first end 234 and second end 236 of the flexible compartment 218. The yoke/impeller 232 may be mounted to a second bearing assembly 222 to provide rotational movement to the helical assembly 214 on an opposing end of the flexible compartment 218. One impeller 216 or more may be mounted to the helical assembly 214 to provide mixing to a fluid within the flexible compartment 218. To facilitate installation of the flexible compartment 218 into the rigid housing 208 a pull handle 220 may be mounted to the second end 236 of the flexible compartment 218 and in some embodiments onto the second bearing assembly 222. The rigid housing 208 may be mounted to a rigid housing support 224 and support wheels 226 may be attached to the rigid housing support 224 to provide mobility to the mixing system 200. In various embodiments, the flexible compartment 218 further comprises at least one port 228 that may protrude through the rigid housing floor 124, 238.

In various embodiments, a user can open the door 110 to the rigid housing 102, 208 for easy installation of the flexible compartment 118, 218. As seen in FIG. 1, when the door 110 move to an open position the top surface 126 of the rigid housing 102, 208 may be completely open on the front face. The top surface 126 may make a "U" perimeter shape that comprises a back portion and two side portions that extend toward the door. While the door 110 is in the open configuration the flexible compartment 118, 218 may be moved into the chamber of the rigid housing 102, 208. The first bearing assembly 106, 204 located on the first end 116, 234 of the flexible compartment 118, 218 may then be inserted onto the drive shaft 120, 240. Additional disclosure relating to mounting the flexible compartment 118, 218 to the drive shaft 120 may be found in US 2017-0183617, filed on Dec. 28 of 2016 which is incorporated herein by specific reference in its entirety. Hangers (not shown) attached to the rigid housing 102, 208 may be hooked onto loops (not shown) on the flexible compartment 118, 218 to further secure the flexible compartment 118, 218 to the top surface 126 of the rigid housing 102, 208. Once the first end 116 of the flexible compartment 118, 218 is secured to the top surface 126 of the rigid housing 102, 208 the second end 236 may slide into the rigid housing floor 124, 238. In various embodiments, the flexible compartment 118, 218 will comprise one port 228 or more and a second bearing assembly 222 that protrude from the exterior of the second end 236 of the flexible compartment 118, 218. Rigid housing openings 122 in the rigid housing floor 124, 238 may be configured to accept the one port 228 or more and second bearing assembly 222, thereby, securing the second end 236 of the flexible compartment 118, 218 to the rigid housing floor 124, 238 of the rigid housing 102, 208. In some embodiments, a closure (not shown) can cover the rigid housing openings 122 to further secure the one port 228 or more and second bearing assembly 222 to the rigid housing floor 124, 238 of the rigid housing 102, 208. In various embodiments, a user can grip the pull handle 220 located at the second end 236 of the flexible compartment 118, 218 to pull the flexible compartment 118, 218 into place within the rigid housing 102, 208.

In various embodiments, once installation has been accomplished a fluid may be fed into the sterile flexible compartment 118, 218 which may require mixing. The motor 104, 202 may be activated using a controller (not shown) which may then rotate the drive shaft 120, 240 which was inserted previously into the first bearing assembly 106. In some embodiments, there may be a single drive shaft 120, 240 that protrudes from the motor 104, 202 and into the sterile flexible compartment 118, 218 and in other embodiments the first bearing assembly 106 will be closed off and have a second drive shaft portion 242 that extends from the first bearing assembly 106. In various embodiments, the drive shaft 120 or second drive shaft portion 242 will mount to a yoke 230 that works to space apart a first line 210 and a second line 212 of a driveline 206. On the second end 236 of the flexible compartment 118, 218 there may be a second bearing assembly 222 comprising a yoke/impeller 232 that operates to suspend the other ends of the first line 210 and the second line 212 as well as provide mixing as it rotates. The second bearing assembly 222 may be designed to provide rotational movement so that rotational to allow the helical assembly 214 to freely rotate as the motor 104, 202 drives the helical assembly 214 from the opposing end. One impeller 216 or more may provide mixing in addition to the yoke/impeller 232.

In various embodiments, an added advantage of the yoke/impeller 232 is to provide very low volume mixing. For example, a bioreaction may require a small volume at the beginning of a reaction and the fluid volume may be increased as the bioreaction matures. Currently available bioreactors have limitations with scale-up which the present embodiment reduces. One impeller 216 or more may be affixed at various locations on the helical assembly 214 when considering optimal scale up for a given bioreactor as well. In some embodiments, the yoke/impeller 232 may maintain a homogenous mix in the fluid at very low volume during a draining process.

Figure 3:
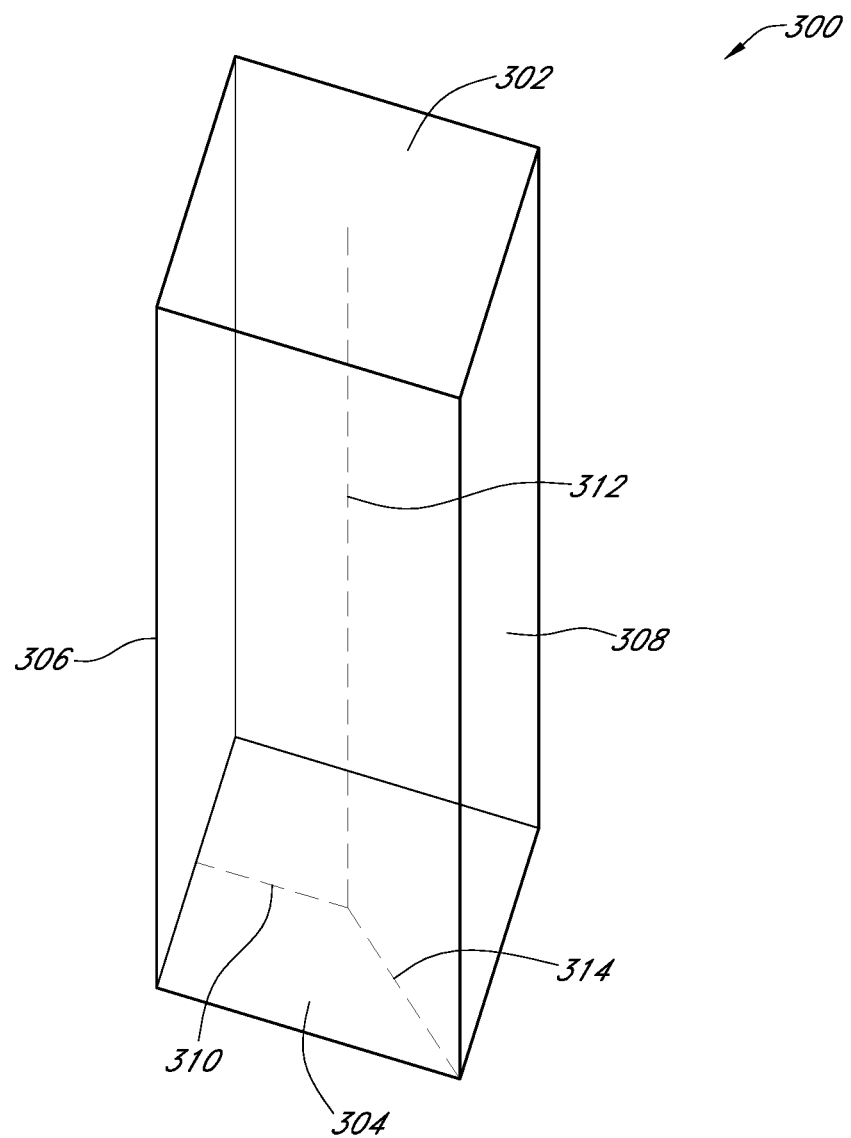
FIG. 3 illustrates a flexible compartment 300 in accordance with one embodiment.

FIG. 3 illustrates a flexible compartment 300 according to various embodiments. The flexible compartment 300 comprises a first end 302, an opposing second end 304, a sidewall 306 connecting the first end 302 and the second end 304, at least three panels 308 joining the first end 302 and the second end 304, a sidewall line 310, a centerline 312, and a cornerline 314.

In various embodiments, the centerline 312 is an indicator of a vertical axis running from the center of the first end 302 to the center of the second end 304 of the flexible compartment 300. For example, the centerline 312 may be placed such that the length from the centerline 312 to opposing panels 308 is equal. In various embodiments, a sidewall line 310 may be an indicator of a plane running from the first end 234 to the second end 304 of the flexible compartment 300 and extend from the centerline 312 to the mid-point of a panel 308. In various embodiments, a cornerline 314 may be an indicator of a plane running form the first end 302 to the second end 304 of the flexible compartment 300 and extend from the centerline 312 to where two panels 308 are joined to form a corner. In various embodiments, the indicators listed above may be used to determine where the helical assembly 214 will reside within the flexible compartment 300 when reducing dead zones and increasing bulk fluid and, thereby, increasing overall mixing efficiency within the mixing system 100, 200.

Figure 4:
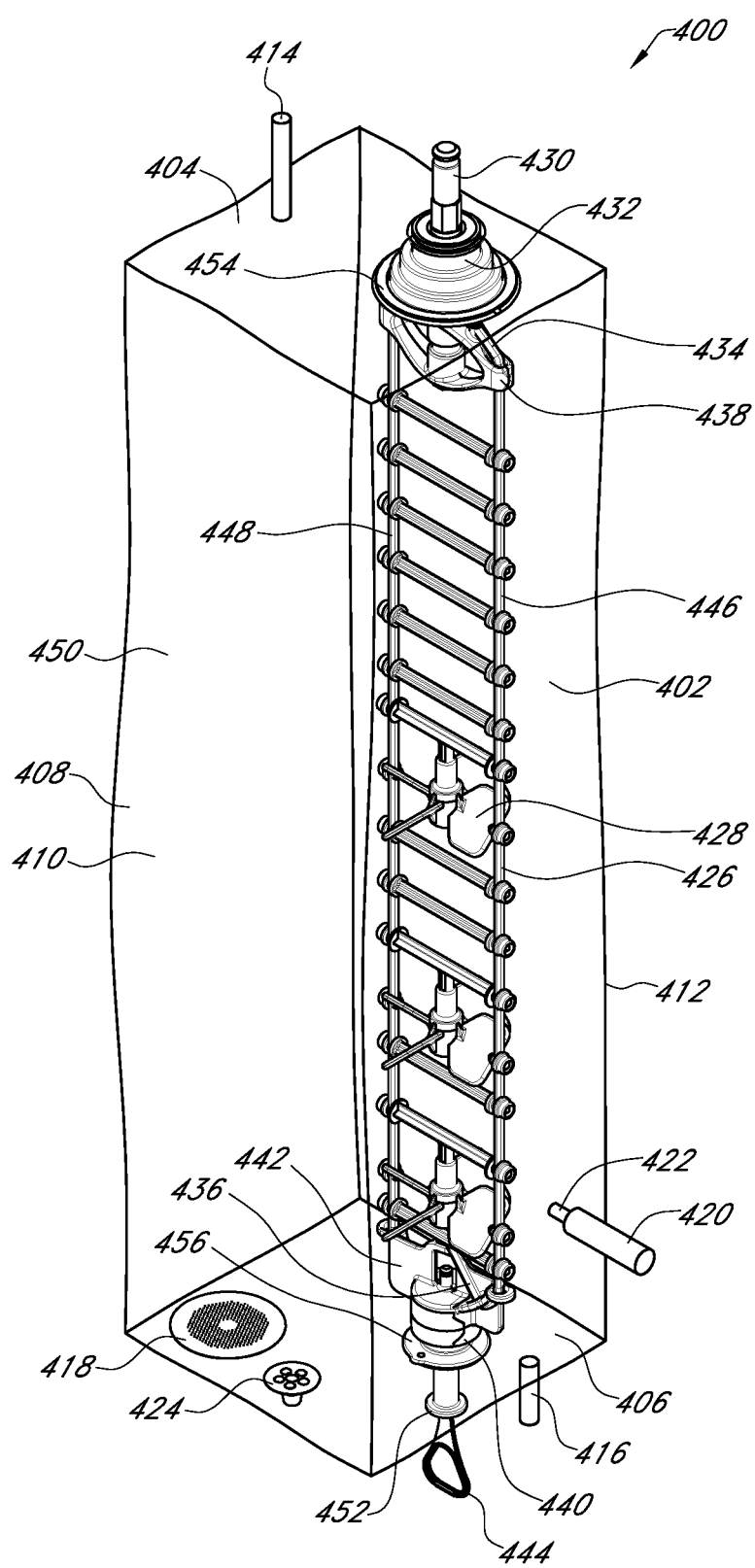
FIG. 4 illustrates a mixing system 400 including a flexible compartment 402 and helical assembly 426 in accordance with one embodiment.

FIG. 4 illustrates a mixing system 400 according to various embodiments. The mixing system 400 comprises a flexible compartment 402 having a first end 404 and an opposing second end 406 that are joined together by a sidewall 408 having at least three panels 410 and sidewall corners 412 where the panels meet. The flexible compartment 402 may further include one or more inlets 414, one or more outlets 416, one or more spargers 418, one or more sensor ports 420 that optionally contain a sensor 422, and a drain 424. In various embodiments a helical assembly 426 may be suspended between the first end 434 and the second end 436 of the flexible compartment 402 and have one or more impellers 428 positioned thereto. In various embodiments, a drive shaft 430 may project into a first bearing assembly 432 and the first bearing assembly 432 may provide a sterile connection between the drive shaft 430 on the exterior of the flexible compartment 402 to a yoke on the interior of the flexible compartment 402. In various embodiments, a second bearing assembly 440 may be positioned on the second end 406 of the flexible compartment 402 and may include a pull handle 444 projecting onto the exterior portion of the flexible compartment 402 and on the opposing/interior portion the second bearing assembly 440 may connect to a yoke/impeller 442. In various embodiments, the helical assembly 426 may be comprised of a first line 446 and a second line 448 that each have a first end 434 connected to a yoke 438 and a second end 436 connected to a yoke/impeller 442 and during operation the rotational movement may be applied to mix a fluid 450 within the flexible compartment 402. In various embodiments, the flexible compartment 402 may include an attachment ring 452 either affixed to or molded as part of the second bearing assembly 222 used can slide into a retention device on the rigid housing 102, 208 during installation. In some embodiments, the design may include a snap ring that fits onto a pin and may slide into the bottom port of the flexible compartment 402.

In various embodiments, the flexible compartment 402 may include one or more inlets 414 and outlets 416. Inlets 414 may be used during the installation process to add a gas to the flexible compartment 402 in order to inflate the flexible compartment 402 to its working volume. Additionally, inlets 414 may be used to introduce dry media, buffers, liquid nutrients, or anything else requiring mixing. An outlet 416 may be used to harvest the contents of the flexible compartment 402 after a mixing process is complete or a bioreaction has achieved a desired state. Additionally, a drain 424 may be used to empty the waste within the flexible compartment 402. There are various ways known in the art for attaching inlets 414, outlets 416, and drains 424. A common technique is weld the component to the flexible compartment 402. For example the component may include a polymer that can be welded to the polymer comprising the flexible compartment 402. US 2017-0183617 includes a list of common weldable materials used to produce flexible compartments 402.

In various embodiments, sensors 422 may be used to monitor the environmental conditions within the flexible compartment 402. There are a variety of sensors and sensor ports 420 available on the market including those described in US 2008-0032389 filed on Mar. 26 of 2007 which is incorporated herein by specific reference in its entirety. Various techniques are described in the above cited reference disclosing ways to bond sensor ports 420 to flexible compartments 402 using welding and adhesion methods.

In various embodiments, the mixing system 400 described herein may be used for cultivating cells and then harvesting the cells in their entirety or harvesting a cell byproduct such as a protein or enzyme. Such bioreactions often require introduction of a gas which is typically done with using a sparger 418 in the field of bioproduction. A variety of sparger 418 designs and their methods of attachment are described in US 2013-0082410 filed on Sep. 28 of 2012 which is incorporated herein by specific reference in its entirety.

In various embodiments, the first bearing assembly 432 and the second bearing assembly 440 may include a first annular sealing flange 454 and a second annular sealing flange 456 that may be sealed to openings on the flexible compartment 402 by welding or adhesive around the perimeter. As disclosed in US 2017-0183617 this allows for rotational movement of a hub while an outer casing remains fixed to the flexible compartment 402 allowing the helical assembly 426 to freely rotate within the flexible compartment 402 while remaining sterile to the exterior.

In various embodiments, an attachment ring 452 may be engageable to a retention device on the rigid housing 102, 208. The retention device may take the form of a bracket or some other physical structure capable of retaining and/or restricting the movement of the attachment ring 452. Generally, during the installation process a user will pull the pull handle 444 into the rigid housing opening 122 in order to facilitate the attachment ring 452 and retention device interaction in order to complete flexible compartment 402 installation.

In various embodiments, the optimal location of the helical assembly 426 relative to the flexible compartment 402 will be along the centerline 312 as depicted in FIG. 4.

Figure 5:
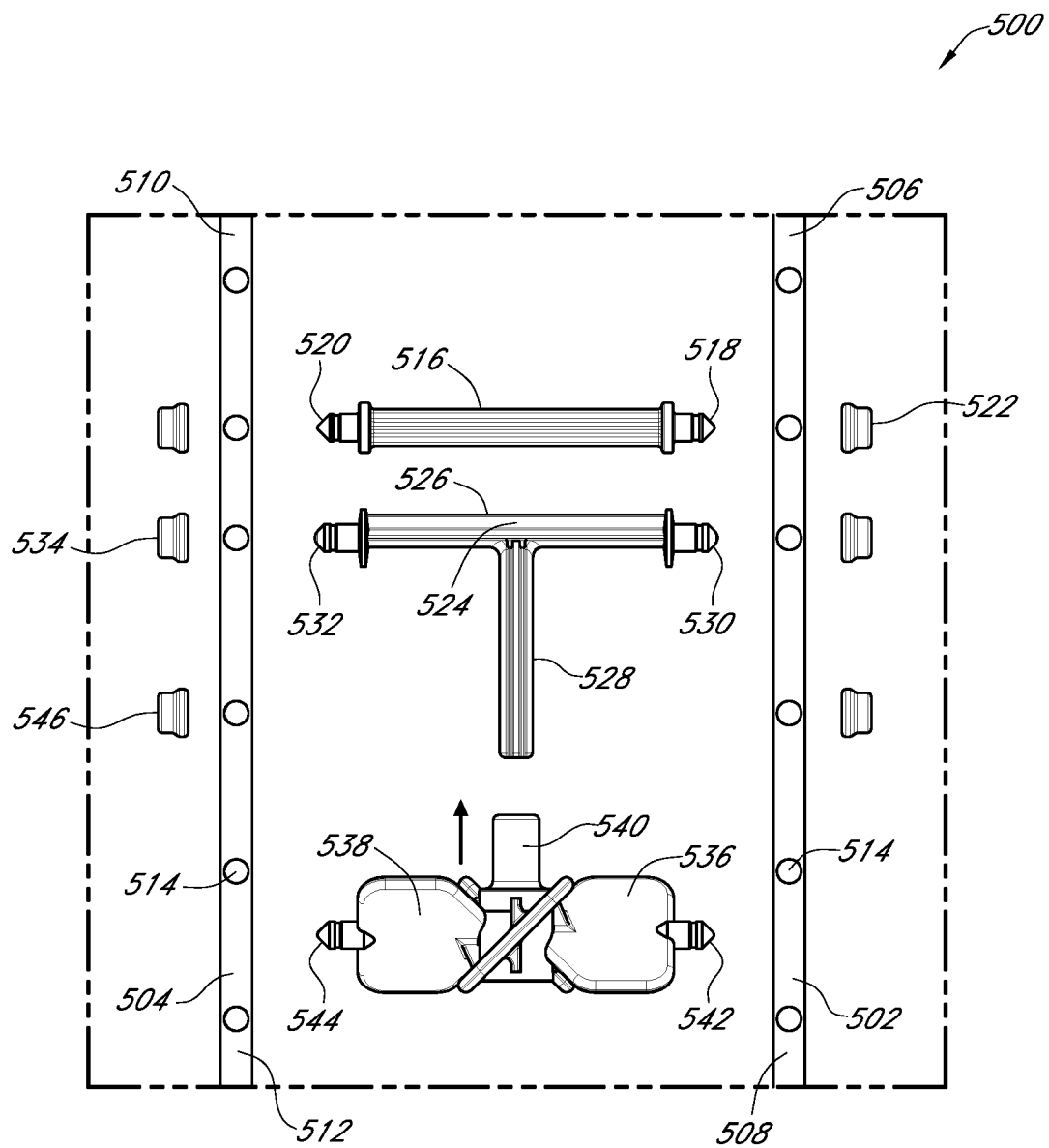
FIG. 5 illustrates an exploded view of a helical assembly 500 in accordance with one embodiment.

FIG. 5 is an illustration of an exploded view of a portion of a helical assembly 500 according to various embodiments. The helical assembly 500 may comprise a first line 502, a second line 504, one or more rungs 516, one or more stabilizers 524, and one or more impellers 536. Each of the lines may include a first end 506, 510 and a second end 508, 512.

In various embodiments, the helical assembly may comprise one or more rungs 516 having a first protrusion 518 that projects through an opening 514 on a first line 502 and a second protrusion 520 that projects through an opening 514 on a second line 504. In some embodiments, rung caps 522 may snap onto the protrusions 518, 520 to secure the rungs 516 to the lines 502, 504.

In various embodiments, the helical assembly 500 may include a stabilizer 524 that includes a crossmember 526 having a first end 530 that projects through an opening 514 on the first line 502 and a second end 532 that projects through an opening 514 on the second line 504. Stabilizer caps 534 may snap onto the ends 530, 532 to secure the stabilizer 524 onto the helical assembly 500. In some embodiments, a stem 528 may project from the center and perpendicular to the crossmember 526.

In various embodiments, an impeller 536 may include fins 538 having a first attachment 542 that projects through an opening 514 on the first line 502 and a second attachment 544 that projects through an opening 514 on the second line 504. In some embodiments impeller caps 546 may snap onto the attachments 542, 544 to secure the impeller 536 onto the helical assembly 500. In various embodiments, a receiver 540 may extend from the center and perpendicular to the impeller 536.

In various embodiments, the receiver 540 may be tubular in nature and accept a stem 528 from the stabilizer 524. The receiver 540 and stem 528 may slide relative to one another as the rotational rate of the helical assembly 500 varies.

Figure 6:
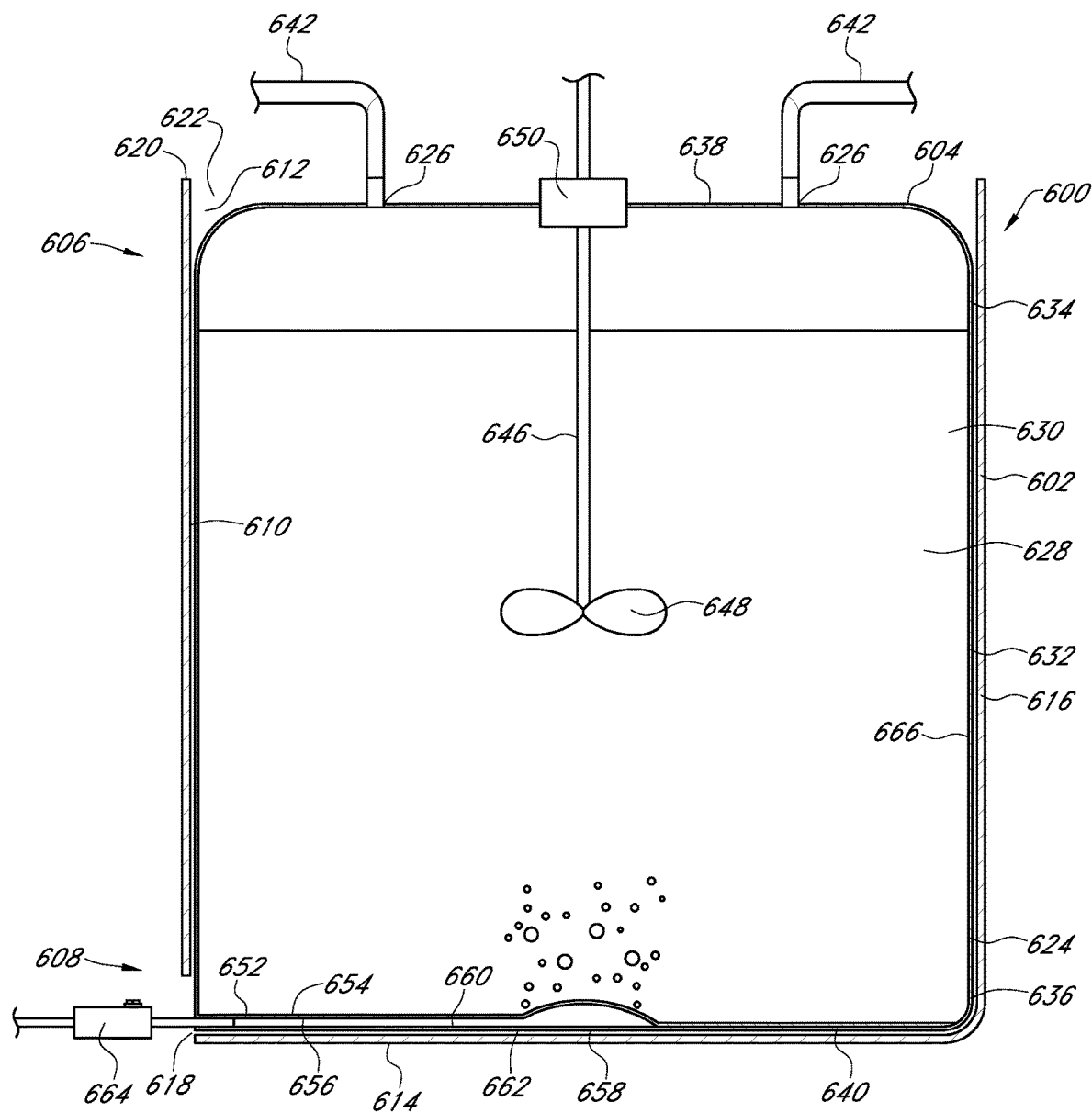
FIG. 6 illustrates a mixing system 600 including a flexible container 604 and sparger in accordance with one embodiment.

FIG. 6 is an illustration of one embodiment of a mixing system 600 incorporating features of the present invention. The mixing system 600 comprises a substantially rigid support rigid support housing 602 in which a flexible container 604 is disposed. Rigid support housing 602 has an upper end 606, a lower end 608, and an interior surface 666 that bounds a compartment 612. Formed at lower end 608 is a floor 614. An encircling sidewall 616 extends up from floor 614 toward upper end 606. As will be discussed below in greater detail, one opening 618 or more can extend through floor 614 or sidewall 616 of rigid support housing 602 so as to communicate with compartment 612. Examples of sparger devices and systems that can be used in the presently disclosed invention are disclosed in U.S. Pat. No. 9,643,133 that issued on May 9, 2017 which is hereby incorporated by specific reference.

Upper end 606 terminates at a lip 620 that bounds an inlet opening 622 to compartment 612. If desired, a cover, not shown, can be mounted on upper end 606 so as to cover inlet opening 622. Likewise, an access opening can be formed at another location on rigid support housing 602 such as through sidewall 616 at second end or through floor 614. The access opening is large enough so that an operator can reach through the access opening to help manipulate and position flexible container 604. The access opening can be selectively closed by a door or cover plate.

It is appreciated that rigid support housing 602 can come in a variety of different sizes, shapes, and configurations. For example, floor 614 can be flat, frustoconical, or have other slopes. Sidewall 616 can have a transverse cross section that is circular, polygonal or have other configurations. Rigid support housing 602 can be insulated and/or jacketed so that a heated or cooled fluid can flow through the jacket for heating or cooling the fluid contained within flexible container 604. Flexible container 604 can be any desired volume such as those discussed below.

As also depicted in FIG. 6, flexible container 604 is at least partially disposed within compartment 612 of support rigid support housing 602. Flexible container 604 comprises a container 624 having one or more ports 626 mounted thereon. In the embodiment depicted, container 624 comprises a flexible bag having an interior surface 610 that bounds a chamber 628 suitable for holding a fluid 630 or other type of material. More specifically, container 624 comprises a side wall 632 that, when container 624 is inflated, can have a substantially circular or polygonal transverse cross section that extends between a first end 634 and an opposing second end 636. First end 634 terminates at a top end wall 638 while second end 636 terminates at a bottom end wall 640.

Container 624 can be comprised of one or more sheets of a flexible, water impermeable material such as a low-density polyethylene or other polymeric sheets having a thickness typically in a range between about 0.1 mm to about 5 mm with about 0.2 mm to about 2 mm being more common. Other thicknesses can also be used. The material can be comprised of a single ply material or can comprise two or more layers that are either sealed together or separated to form a double wall container. Where the layers are sealed together, the material can comprise a laminated or extruded material. The laminated material can comprise two or more separately formed layers that are subsequently secured together by an adhesive.

The extruded material can comprise a single integral sheet that comprises two or more layers of different material that are each separated by a contact layer. All of the layers are simultaneously co-extruded. One example of an extruded material that can be used in the present invention is the HyQ CX3-9 film available from HyClone Laboratories, Inc. out of Logan, Utah. The HyQ CX3-9 film is a three-layer, 9 mil cast film produced in a cGMP facility. The outer layer is a polyester elastomer coextruded with an ultra-low density polyethylene product contact layer. Another example of an extruded material that can be used in the present invention is the HyQ CX5-14 cast film also available from HyClone Laboratories, Inc. The HyQ CX5-14 cast film comprises a polyester elastomer outer layer, an ultra-low density polyethylene contact layer, and an EVOH barrier layer disposed therebetween. In still another example, a multi-web film produced from three independent webs of blown film can be used. The two inner webs are each a 4 mil monolayer polyethylene film (which is referred to by HyClone as the HyQ BM1 film) while the outer barrier web is a 5.5 mil thick 6-layer co-extrusion film (which is referred to by HyClone as the HyQ BX6 film).

The material can be approved for direct contact with living cells and be capable of maintaining a solution sterile. In such an embodiment, the material can also be sterilizable such as by ionizing radiation. Examples of materials that can be used in different situations are disclosed in U.S. Pat. No. 6,083,587 that issued on Jul. 4, 2000 and U.S. Patent Publication No. US 2003/0077466 A1, published Apr. 24, 2003 that are each hereby incorporated by specific reference.

In one embodiment, container 624 comprises a two-dimensional pillow style bag wherein two sheets of material are placed in overlapping relation and the two sheets are bounded together at their peripheries to form internal chamber 628. Alternatively, a single sheet of material can be folded over and seamed around the periphery to form internal chamber 628. In another embodiment, container 624 can be formed from a continuous tubular extrusion of polymeric material that is cut to length and the ends seamed closed.

Figure 7:
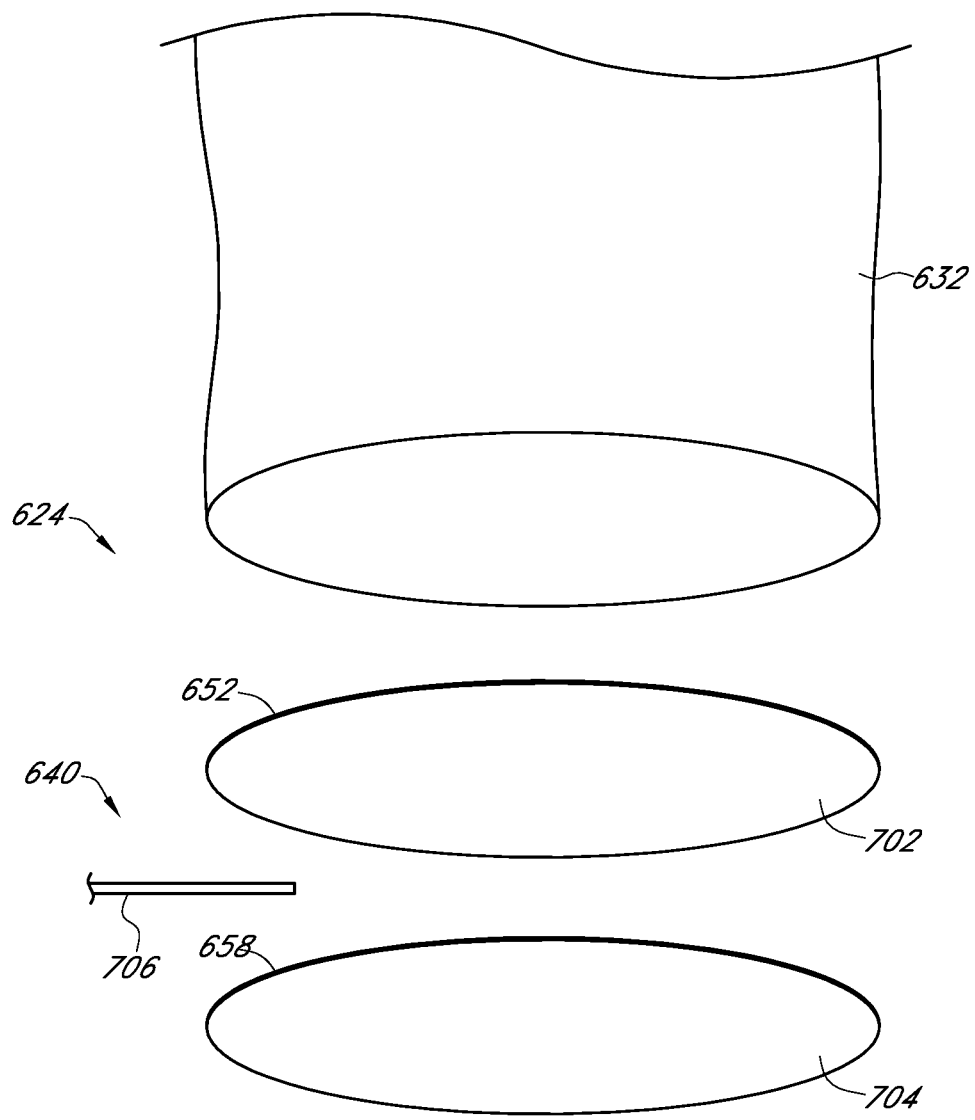
FIG. 7 illustrates a sparger 700 design in accordance with one embodiment.

In still other embodiments, container 624 can comprise a three-dimensional bag that not only has an annular side wall but also a two-dimensional top end wall 638 and a two dimensional bottom end wall 640. For example, three-dimensional container 624 can comprise sidewall 616 formed from a continuous tubular extrusion of polymeric material that is cut to length, such as shown in FIG. 7. A circular top end top end wall 638 and bottom end wall 640 can then be welded to opposing ends of sidewall 616. In yet another embodiment, three-dimensional container 624 can be comprised of a plurality of discrete panels, typically three or more, and more commonly between four to six. Each panel can be substantially identical and comprises a portion of side wall 632, top end wall 638, and bottom end wall 640 of container 624. The perimeter edges of adjacent panels are seamed together to form container 624. The seams are typically formed using methods known in the art such as heat energies, RF energies, sonics, or other sealing energies. In alternative embodiments, the panels can be formed in a variety of different patterns.

It is appreciated that container 624 can be manufactured to have virtually any desired size, shape, and configuration. For example, container 32 can be formed having chamber 628 sized to 10 liters, 30 liters, 100 liters, 250 liters, 500 liters, 750 liters, 1,000 liters, 1,500 liters, 3,000 liters, 5,000 liters, 10,000 liters or other desired volumes. Chamber 628 can also have a volume in a range between about 10 liters to about 5,000 liters or about 30 liters to about 1,000 liters. Any other ranges selected from the above volumes can also be used. Although container 624 can be any shape, in one embodiment container 624 is specifically configured to be complementary to or substantially complementary to compartment 612 of rigid support housing 602.

In any embodiment, however, it is typically desirable that when container 624 is received within compartment 612, container 624 is generally uniformly supported by support rigid support housing 602. Having at least generally uniform support of container 624 by rigid support housing 602 helps to preclude failure of container 624 by hydraulic forces applied to container 624 when filled with fluid.

Although in the above discussed embodiment container 624 is in the form of a flexible container 604, in alternative embodiments it is appreciated that container 624 can comprise any form of collapsible container, flexible container 604, or semi rigid container. Furthermore, in contrast to having a closed top end wall 638, container 624 can comprise an open top liner. Container 624 can also be transparent or opaque and can have ultraviolet light inhibitors incorporated therein.

Mounted on top end wall 638 are a plurality of ports 626 that are in fluid communication with chamber 628. Although two ports 626 are shown, it is appreciated that one or three or more ports 626 can be present depending on the intended use of container 624. As such, each port 626 can serve a different purpose depending on the type processing to be undertaken. For example, ports 626 can be coupled with a tube 642 for dispensing fluid or other components into chamber 628 or withdrawing fluid from chamber 628. In addition, such as when container 624 is used as a bioreactor for growing cells or microorganisms, ports 626 can be used to provide various probes, such as temperature probes, pH probes, dissolved oxygen probes, and the like, access to chamber 628. It is appreciated that ports 626 can come in a variety of different configurations and can be placed at any number of different locations on container 624, including sidewall 616 and bottom end wall 640.

Although not required, in one embodiment means are provided for mixing fluid 630 within chamber 628. The means for mixing can be in the form of a mixing assembly. By way of example and not by limitation, in one embodiment as shown in FIG. 6 a drive shaft 646 projects into chamber 628 and has an impeller 648 mounted on the end thereof. A dynamic seal 650 forms a seal between drive shaft 646 and container 624. External rotation of drive shaft 646 facilitates rotation of impeller 648 that mixes and/or suspends fluid 630 within a chamber 628. Specific examples of how to incorporate a rotational mixing assembly into a flexible container are disclosed in U.S. Pat. No. 7,384,783 that issued Jun. 10, 2008 and U.S. Pat. No. 7,682,067 that issued on Mar. 23, 2010, which are incorporated herein by specific reference.

In yet another alternative embodiment of the means for mixing or the mixing assembly, mixing can be accomplished by vertically reciprocally moving a vertical mixer within chamber 628. Further disclosure with regard to the assembly and operation of vertical mixer is disclosed in U.S. Patent Publication No. 2006/0196501, published Sep. 7, 2006, which is incorporated herein by specific reference. In yet other embodiments, it is appreciated that the mixing can be accomplished by simply circulating fluid through chamber 628 such as by using a peristaltic pump to move fluid in and out of chamber 628 by rotating a magnetic impeller or stir bar within container 624 and/or by injecting sufficient gas bubbles within the fluid to mix the fluid. Other conventional mixing techniques can also be used.

Continuing with FIG. 6, bottom end wall 640 has a plurality of spargers incorporated therein. Specifically, bottom end wall 640 comprises a first sheet 652 having a first side face 654 and an opposing second side face 656. The first sheet 652 overlays a second sheet 658 that likewise has a first side face 660 and an opposing second side face 662. First sheet 652 and second sheet 658 typically comprise flexible polymeric sheets such as those discussed above with regard to container 624. As discussed above with regard to bottom end wall 640, the first sheet 652 can comprise a continuous sheet that is welded to the side wall 632 around a perimeter edge 702 as depicted in FIG. 7. Alternatively, first sheet 652 can comprise an integral portion of sidewall 616 or can comprise a plurality of separate sheets secured together that are either attached to or are an integral portion of sidewall 616. Second sheet 658 can be welded to second side face 656 of first sheet 652 and/or welded to sidewall 616, such as along a perimeter edge 704 of the second sheet 658. In other embodiments, second sheet 658 can be welded to or comprise an integral portion of sidewall 616, as discussed above with regard to first sheet 652, while the first sheet 652 is welded or otherwise secured to first side face 660 of second sheet 658 and/or sidewall 616.

Figure 8:
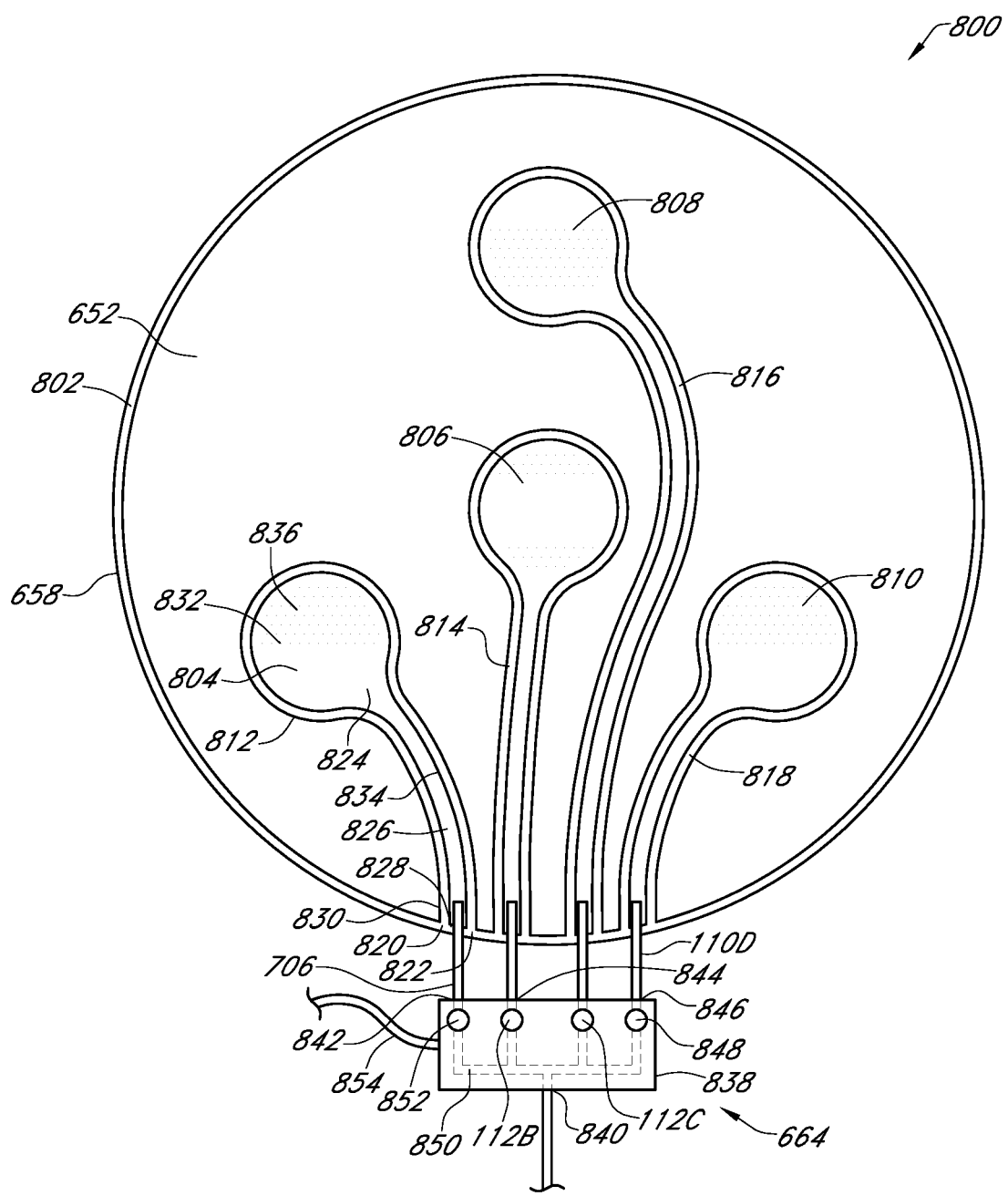
FIG. 8 illustrates a sparger 800 in accordance with one embodiment.

Depicted in FIG. 8 is a top plan view of first sheet 652 overlaying second sheet 658. In this embodiment, the first sheet 652 and the second sheet 658 are welded together by a weld line 802. Weld line 802, as with other weld lines discussed herein, can be formed using any conventional technique such as laser welding, sonic welding, heat welding, or the like. Weld line 802 is shown as welding together the perimeter or outside edges of the first sheet 652 and the second sheet 658 but can be formed radially inward from one or both of the perimeter edges or at other locations. As also shown in FIG. 8, four separate spargers 804, 806, 808, 810 are formed by producing other weld lines between the first sheet 652 and the second sheet 658.

For example, spargers 804, 806, 808, 810 are formed by forming weld lines 812, 814, 816, 818 starting at first locations 820 located at or adjacent to the perimeter edge of first sheet 652 and/or second sheet 658 and extending into the interior of the first sheet 652 and the second sheet 658 along a predetermined path for the sparger 804 and then circles back to a second location 822 at or adjacent to the perimeter edge of the first sheet 652 and/or the second sheet 658 adjacent to first location 820. Weld line 812 bounds a perimeter of a sparger pathway 824 which is the area bounded between the first sheet 652 and the second sheet 658 and partially encircled by weld line 812. In the embodiment depicted, sparger pathway 824 comprises a gas transfer path 826 that extends from a first end 830 to an opposing second end 834. An opening 828 is formed at first end 830 between the first location 820 and the second location 822 and between the first sheet 652 and the second sheet 658 through which a gas can be fed into gas transfer path 826. Sparger pathway 824 also comprises a sparging area 832 formed at second end 834 that is in fluid communication with gas transfer path 826. In the embodiment depicted, gas transfer path 826 is a narrow elongated path while sparging area 832 forms an enlarged circular area. Other configurations can also be used.

A plurality of perforations 836 extend through first sheet 652 of sparging area 832 so that gas can pass along gas transfer path 826, into sparging area 832 and then out through perforations 836 to form gas bubbles within fluid 630 disposed within chamber 628. Spargers 806, 808, 810 are similarly formed with like reference characters being used to identify like elements. By using this technique, a plurality of discrete spargers can be easily formed on container 624. Each sparger can be disposed at any desired location and be any desired size, shape or configuration. Likewise, although four spargers are shown, it is appreciated that any number of spargers such as 1, 2, 3, 5, or more can be formed with the first sheet 652 and the second sheet 658. The sparging areas can be uniformly distributed over the first sheet 652 and the second sheet 658 or can be located at defined locations for optimal sparging. For example, a sparger can be disposed directly below the means for mixing such that the mixing or movement of fluid 630 produced by the mixer helps to entrain the gas bubbles within fluid 630.

In some embodiments, each sparger can have the same number of perforations 836 and all perforations 836 can be the same size and shape. In alternative embodiments, perforations 836 can be different between two or more different spargers. For example, different spargers can have different numbers, sizes, and/or shapes of perforations 836 to optimize performance in different situations. Larger perforations 836 produce larger gas bubbles that may be optimal for stripping CO2 from fluid 630 whereas smaller perforations produce smaller bubbles that may be preferred for oxygenating fluid 630. Likewise, increasing the number of perforations 836 may be helpful in causing the bubbles to mix the fluid and/or increase stripping or oxygenation. In other embodiments, it is appreciated that one or more of spargers 804, 806, 808, 810 can have combinations of different perforations 836. For example, a single sparger can have both small and large perforations 836. In one embodiment, the smaller bubbles are formed from perforations 836 typically having a diameter of less than 0.8 mm, 0.4 mm or 0.2 mm, 0.1 mm while the large bubbles are formed from perforation typically having a diameter greater than 1.5 mm, 0.8 mm, 0.4 mm or 0.15 mm. Perforations of other diameters can also be used. The size of the perforation and resulting bubbles depends on the intended use and the size of container 624. For example, the large bubbles are typically larger when processing a large volume of fluid in a large container than when processing a relatively small volume of fluid in a small container. The variance or delta between the diameter of the perforations for the small bubbles and the perforations for the large bubbles is typically at least 0.15 mm, 0.3 mm, 0.5 mm or 1 mm and is often within ±0.1 mm or ±0.5 of these values. Other variances can also be used.

As discussed below in greater detail, spargers 804, 806, 808, 810 can simultaneously operate or, alternatively, a manifold or other regulator can be used so that one or more of the spargers can be operated while the other spargers are not operated. Accordingly, by having different spargers with different perforations 836, select spargers can be used in different situations or times to optimize performance.

In some embodiments, it is appreciated that gas transfer gas transfer path 826 of sparger 804 is not required. For example, perforations 836 can be formed through first sheet 652 overlying gas transfer path 826 so as to convert gas transfer path 826 in a portion of sparging area 832. It is appreciated that perforations 836 can be formed using any conventional techniques. For example, perforations 836 can be formed as part of the manufacturing process for the sheet or can be subsequently produced by punches or other techniques. In one embodiment, one or more lasers can be used to form perforations 836. An advantage of using a laser is that perforations 836 can be formed at precise locations and with a precise diameter so that bubbles can be formed having a precise, predefined size. Furthermore, when a laser is used to form a perforation, the material melted by the laser gathers around the perimeter edge of the perforation, thereby reinforcing the perforation and helping to prevent rupture of the sheet.

In one embodiment of the present invention, a manifold can be used for controlling the gas flow to one or more of spargers 804, 806, 808, 810. For example, depicted in FIG. 8 is one embodiment of a manifold 664 incorporating features of the present invention. Manifold 664 comprises a body 838 having a gas inlet port 840 and a plurality of gas outlet ports 842, 844, 846, 848. Gas outlet ports 842, 844, 846, 848 are in parallel communication with gas inlet port 840 by way of a forked flow path 850. A gas source, such as a compressor or a canister of compressed gas, is fluid coupled with gas inlet port 840. The gas can be air, oxygen, or any other gas or combination of gases. Gas lines 706 extend from gas outlet ports 842, 844, 846, 848, respectively, to a corresponding openings 828 at first end 830 of each sparger 804, 806, 808, 810, respectively. Gas lines 706 can be welded between the first sheet 652 and the second sheet 658 at openings 828 so as to seal openings 828 closed. Gas lines 706 can comprise flexible or rigid tubes and can be integrally formed with or separately attached to body 838.

Valves 852 are mounted on body 838 and control the flow of gas to each gas line 706, respectively. In one embodiment, valves 852 can be electrical valves, such as solenoid valves, that can be used to open, close, or restrict the flow of gas to spargers 804, 806, 808, 810. In this embodiment, electrical wiring 854 can couple to valves 852 for controlling their operation. In other embodiments, valves 852 can comprise valves that are operated manually, hydraulically, pneumatically, or otherwise. By using manifold 664, different spargers or different combinations of spargers can be used at different times to optimize performance as discussed above.

Figure 9:
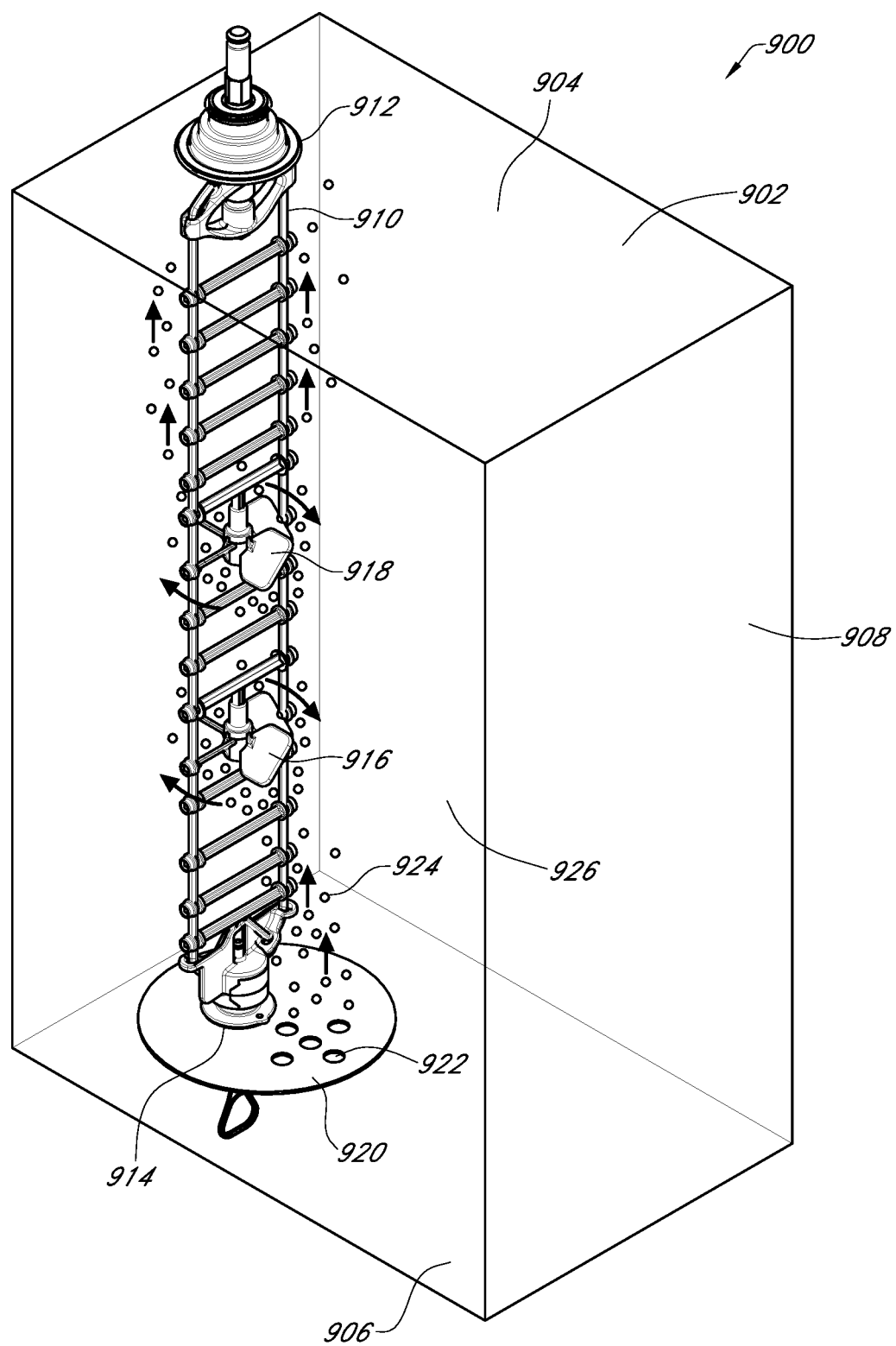
FIG. 9 illustrates a mixing system 900 including a flexible compartment 902 and offset drive shaft 910 in accordance with one embodiment.

FIG. 9 illustrates a mixing system 900 according to various embodiments. The mixing system 900 may comprise a flexible compartment 902 having a first end 904, a second end 906, and a sidewall 908, an offset drive shaft 910 being disposed within the flexible compartment 902 and having a first bearing assembly 912 and a second bearing assembly 914 with a first impeller 916 affixed to the first end 904 and the second end 906 of the flexible compartment 902 respectively and a first impeller 916 and a second impeller 918 affixed to the drive shaft 910 where the flexible compartment 902 further includes a sparger 920 having at least one perforation 922 designed to release bubbles 924 into a fluid 926.

In various embodiments, the sparger 920 releases a gas into the fluid 926 to add dissolved oxygen to the fluid 926. The location of the sparger 920 on the second end 906 of the flexible compartment 902 may be selected so that the gas bubbles 924 optimally interact with the first impeller 916 and the second impeller 918. For example, if a bioreaction requires a specified amount of dissolved oxygen the mixing system 900 can be optimized for residence time of the bubble 924 within the fluid by re-entrainment of the bubbles 924 by the impellers 916, 918. This can be accomplished by adjusting the position of the sparger 920 so that all the bubbles 924 are re-entrained, none of the bubbles 924 are re-entrained, or a specific percentage of the bubbles 924 are re-entrained. For example, the sparger 920 may be moved further away from the second bearing assembly 914 which will make it less likely for the gas bubbles 924 to be re-entrained. In various embodiments, 0%, 10%, 20%, 30%, 40%, 50%, 60%, 70%, 80%, 90%, or 100% of the gas bubbles 924 are re-entrained once by the first impeller 916 and/or second impeller 918 or in any combination. In various embodiments, the rate of impeller rotation may be adjusted to impact the amount of re-entrainment occurring in the mixing system 900. The selection of bubble 924 diameter and impeller properties in combination may also impact the residence time of the bubbles 924.

In various embodiments, the diameter and quantity of the perforations 922 can be selected to optimize the operational characteristics of the mixing system 900 based on the cell type being grown. For example, if residence time needs to be increased in a mixing system 900 to achieve a desired dissolved oxygen content in the fluid 926 the perforations 922 may be smaller to create smaller gas bubbles 924.

Residence time may also increase if the sparger 920 location and properties are selected in conjunction with the location of the impellers on the drive shaft 910 for more or less re-entrainment as required by the desired bioreaction.

In various embodiments, a scalable mixing system 900 may include two or more mixing systems 900 as shown in FIG. 9 where the systems may vary in volume. The volumes may range between a test size of less than 50 liters and a commercial size of greater than 50 liters. The volumes may be selected based on scale up/down cost. For example, the optimal conditions for producing a product using a given cell type may be determined in the smaller test volume size so that outcomes can be predicted in expensive commercial systems without having to expend the resources on the larger volume reaction for optimization. In some embodiments, the impeller tip speed (shear) and power input per volume may be kept constant between the two or more mixing systems 900 while the quantity of impellers and their diameters may vary (See FIG. 23). In some embodiments the sparger 920 location and number and size of the perforation 922 may vary between the test size and the commercial size mixing systems 900.

Figure 10:
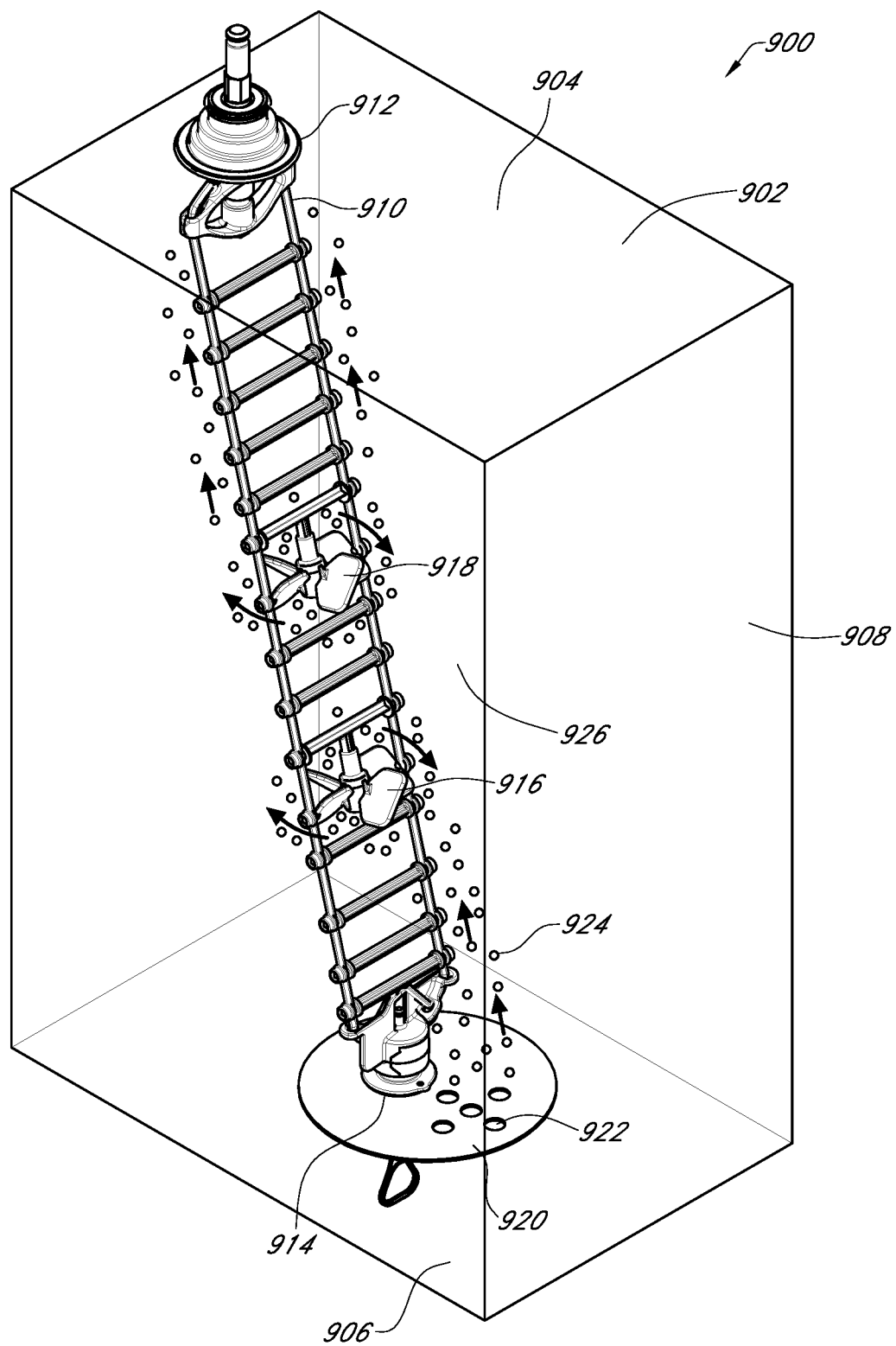
FIG. 10 illustrates a mixing system 1000 including a flexible compartment 902 having an offset and angled drive shaft 910 in accordance with one embodiment.

FIG. 10 illustrates a mixing system 1000 according to various embodiments. The mixing system 900 may comprise a flexible compartment 902 having a first end 904, a second end 906, and a sidewall 908, an offset drive shaft 910 being disposed within the flexible compartment 902 and having a first bearing assembly 912 and a second bearing assembly 914 with a first impeller 916 affixed to the first end 904 and the second end 906 of the flexible compartment 902 respectively and a first impeller 916 and a second impeller 918 affixed to the drive shaft 910 where the flexible compartment 902 further includes a sparger 920 having at least one perforation 922 designed to release bubbles 924 into a fluid 926.

In various embodiments, the drive shaft 910 may be both angled and offset within the flexible compartment 902. Such a configuration will change the operational parameters of the bioreaction by altering the amount of bubble 924 re-entrainment that occurs. For example, if the sparger 920 is positioned near the second bearing assembly 914 the first impeller 916 may re-entrain the bubbles 924 while the second impeller 918 may not contact as many bubbles 924 for re-entrainment. Therefore, the dissolved oxygen content within the fluid 926 can be altered depending on the angle of the drive shaft 910. Additionally, the baffling effects of the rectangular shaped flexible compartment 902 can be increased, decreased, or mixing patterns completely altered based on the amount of offset and angled of the drive shaft 910 within the flexible compartment 902.

Figure 11:
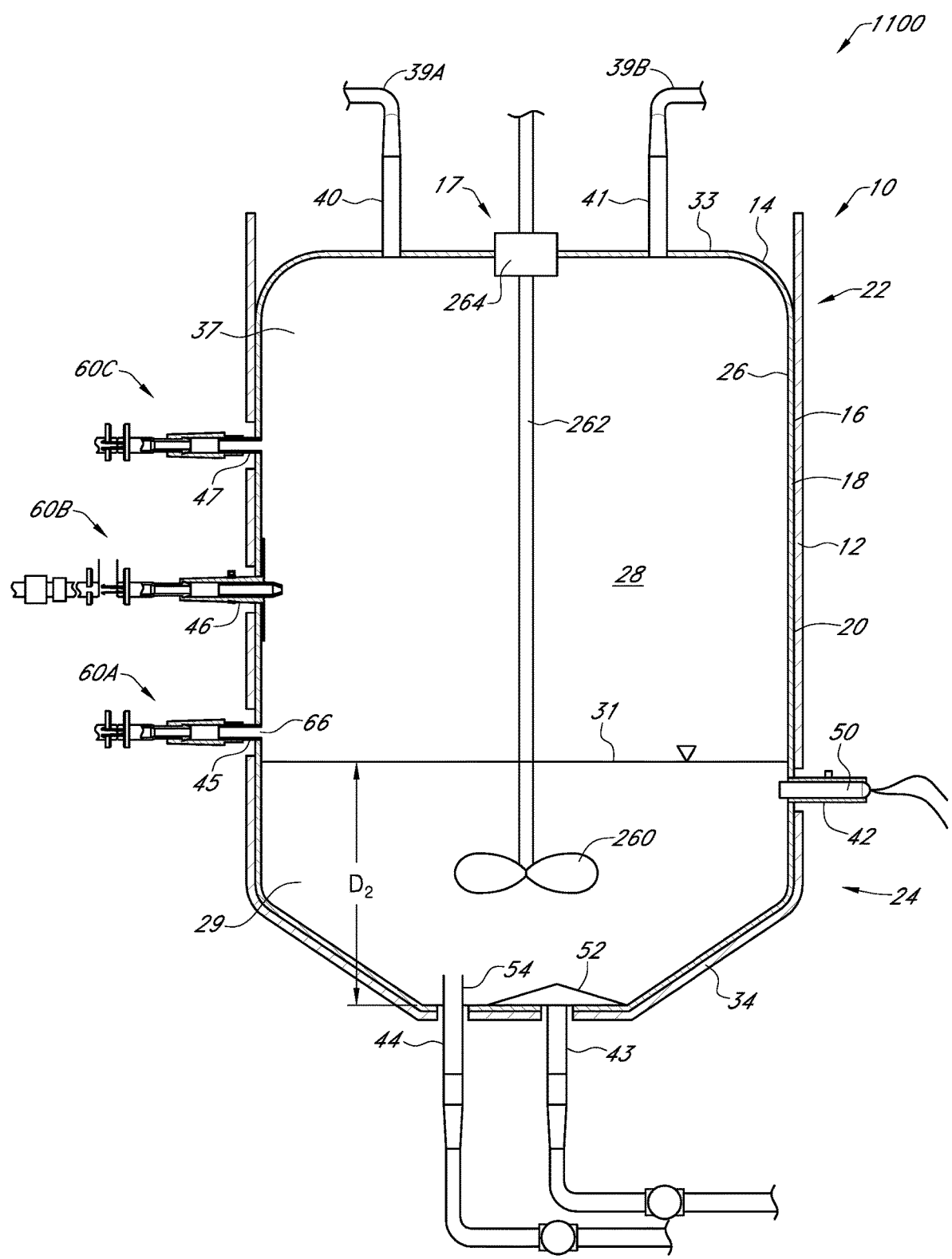
FIG. 11 illustrates a mixing system 1100 including a gas delivery system in accordance with one embodiment.

FIG. 11 illustrates a mixing system 1100 including systems and methods for gas stream mass transfer according to various embodiments. Although gas stream mass transfer is primarily discussed herein with regard to oxygenating a biological culture, the same methods and systems can also be used for oxygenating other types of liquids, such as those mentioned above. In addition, as discussed below in greater detail, the inventive methods and systems are not limited to oxygenating a fluid but can be used with other gases for affecting any type of mass transfer into a liquid and/or out of a liquid.

Gas stream mass transfer has a number of processing advantages when it is used for oxygenating a biological culture within a reactor container, particularly over conventional sparging techniques. Where a reactor container is being designed to process a culture of cells or microorganisms over a relatively large change in fluid volume, the diameter of the container typically needs to be relatively large to maintain geometry and height requirements. As the diameter of the container increases with respect to volume, the depth of the culture within the container decreases. As a result, for very small volumes of culture within the container, such as when the initial volume of culture is transferred into the container, the resident time for the oxygenating bubbles that are typically sparged into the culture from the floor of the container is insufficient to properly oxygenate the culture. That is, because the depth of culture is so shallow, the oxygenating bubbles are not within the culture for a sufficient period of time to fully oxygenate the culture as the bubbles travel from the sparger to the top surface of culture. Likewise, the resident time for the larger sparged bubbles used to strip out the $CO_2$ is also insufficient to fully remove the unwanted $CO_2$ from the culture. This problem is further compounded by the fact that the $CO_2$ gas is heavier than air so that the $CO_2$ lays like a blanket over the top surface of the culture, thereby further hampering oxygenation of the culture and removing $CO_2$.

In contrast to sparging which becomes more efficient as the depth of the culture increases, gas stream oxygenation or mass transfer, which is accomplished by blowing a stream of air or other gas containing oxygen over the top surface of the culture, become more efficient as the depth of the culture or other fluid being processed decreases. Thus, gas stream oxygenation is particularly useful for shallow depth cultures disposed within a reactor; including reactors that start with a small volume and increase to a large volume. In addition, sparging is known to produce unwanted foam on the top surface of cultures, especially when the spargers used generate very small bubbles (sub millimeter diameter). In contrast, gas stream mass transfer produces minimal foaming and can assist in the reducing the vessel foam generation by reducing the amount of traditional sparging required. Furthermore, gas stream oxygenation prevents the formation of a $CO_2$ blanket on the surface of the culture. As such, the gas on the surface of the culture is both well controlled and well mixed, permitting the $CO_2$ to dissipate out of the culture, mix into the head space of the reactor, and leave via the system exhaust port. The interaction of the gas stream oxygenation with the system liquid also helps directly facilitate stripping $CO_2$ from the culture. Accordingly, for relatively shallow depth cultures, gas stream oxygenation can be used to both oxygenate the culture and remove $CO_2$ from the culture, in some cases eliminating the need for traditional sparging in certain forms of the invention.

As the depth of a culture within a reactor increases, the efficiency of oxygenating the culture at the bottom of the reactor through gas stream oxygenation decreases. Accordingly, as the depth of the culture increases, dissolved $O_2$ sensors or other parameters or mechanisms can be used to determine when sparging or other methods of oxygenation should be activated. That is, as the depth of the culture increases, sparging can be activated such as through stepped increments or through continuous gradual increase so as to ensure that the culture is always properly oxygenated. The applied gas stream oxygenation can decrease as sparging increases or can remain constant. Even if the gas stream is not fully oxygenating the culture, the gas stream is still equilibrating the upper region of the culture and preventing $CO_2$ blanketing which in turn assists in traditional sparge operation. Thus, even for relatively deep volumes of culture, gas stream oxygenation can continue to be used in conjunction with sparging or other methods of oxygenation. It should be appreciated that an electronic controller could be used to automatically activate and/or regulate sparging and gas flow based on sensor readings.

Examples of systems will now be discussed that can be used in performing gas stream oxygenation/mass transfer. Additional examples of headspace air flow devices and systems that can be used in the presently disclosed invention are disclosed in U.S. Pat. No. 9,388,375 that issued on Jul. 12, 2016 which is hereby incorporated by specific reference. Depicted in FIG. 11 is one embodiment of a reactor system 10 incorporating features of the present invention. In general, reactor system 10 comprises a support housing 12 that bounds a chamber 14, a container assembly 16 disposed within chamber 14 and a mixing system 17 coupled with container assembly 16. Support housing 12 typically comprises a rigid tank, such as a metal tank. The tank can be jacketed for controlling the temperature of the culture within container assembly 16. Support housing 12 can be any desired size, shape, or configuration that will properly support container assembly 16, as discussed below.

With continued reference to FIG. 11, container assembly 16 comprises a container 18 having a side 20 that extends from an upper end 22 to an opposing lower end 24. Upper end 22 terminates at an upper end wall 33 while lower end 24 terminates at a lower end wall 34. Container 18 also has an interior surface 26 that bounds a compartment 28. Compartment 28 is configured to hold a fluid. The fluid can comprise a biological culture which comprises cells or microorganisms, media, and other nutrients and additives. Any other type of fluid can also be used that requires mass transfer with a gas. For example, the fluid can be a chemical, biological fluid, food product, or other fluid. For the example herein, the fluid will be discussed as biological culture 29. Culture 29 has a top surface 31. A head space 37 is disposed within compartment 28 and is bounded between top surface 31 of culture 29 and upper end wall 33.

In the embodiment depicted, container 18 comprises a flexible bag that is comprised of a flexible, water impermeable material such as a low-density polyethylene or other polymeric sheets or film having a thickness in a range between about 0.1 mm to about 5 mm with about 0.2 mm to about 2 mm being more common. Other thicknesses can also be used. The material can be comprised of a single ply material or can comprise two or more layers which are either sealed together or separated to form a double wall container. Where the layers are sealed together, the material can comprise a laminated or extruded material. The laminated material comprises two or more separately formed layers that are subsequently secured together by an adhesive. Examples of extruded material that can be used in the present invention include the HyQ CX3-9 and HyQ CX5-14 films available from HyClone Laboratories, Inc. out of Logan, Utah. The material can be approved for direct contact with living cells and be capable of maintaining a solution sterile. In such an embodiment, the material can also be sterilizable such as by ionizing radiation. Prior to use, container assembly 16 is typically sealed closed and sterilized so that compartment 28 is sterile prior to the introduction of culture 29.

In one embodiment, container 18 can comprise a two-dimensional pillow style bag. In another embodiment, container 18 can be formed from a continuous tubular extrusion of polymeric material that is cut to length. The ends can be seamed closed or panels can be sealed over the open ends to form a three-dimensional bag. Three-dimensional bags not only have an annular sidewall but also a two dimensional top end wall and a two dimensional bottom end wall. Three dimensional containers can comprise a plurality of discrete panels, typically three or more, and more commonly four or six. Each panel is substantially identical and comprises a portion of the sidewall, top end wall, and bottom end wall of the container. Corresponding perimeter edges of each panel are seamed together. The seams are typically formed using methods known in the art such as heat energies, RF energies, sonics, or other sealing energies.

In alternative embodiments, the panels can be formed in a variety of different patterns. Further disclosure with regard to one method of manufacturing three-dimensional bags is disclosed in United States Patent Publication No. US 2002-0131654 A1, published Sep. 19, 2002, which is incorporated herein by specific reference in its entirety.

It is appreciated that container 18 can be manufactured to have virtually any desired size, shape, and configuration. For example, container 18 can be formed having a compartment sized to 10 liters, 30 liters, 100 liters, 250 liters, 500 liters, 750 liters, 1,000 liters, 1,500 liters, 3,000 liters, 5,000 liters, 10,000 liters or other desired volumes. The size of the compartment can also be in the range between any two of the above volumes. Although container 18 can be any shape, in one embodiment container 18 is specifically configured to be generally complementary to chamber 14 of support housing 12 in which container 18 is received so that container 18 is properly supported within chamber 14.

Although in the above discussed embodiment container 18 is depicted as a flexible bag, in alternative embodiments it is appreciated that container 18 can comprise any form of collapsible container or semi-rigid container. In still other embodiments, container 18 can be rigid and support housing 12 can be eliminated.

Continuing with FIG. 11, formed on container 18 are examples of a plurality of different ports that can be mounted thereon with each of the ports communicating with compartment 28. Specifically, mounted on upper end wall 33 are access ports 40 and 41 having lines 39A and B coupled therewith, respectively. Access ports 40 and 41 can be used for delivering gas, media, cultures, nutrients, and/or other components into container 18 and can be used for withdrawing culture 29 or gas from within head space 37. For example, in some forms of the invention, port 40 can be used as a gas inlet into head space 37 and port 41 can be used as a gas outlet from head space 37. Any desired number of access ports can be formed on container 18. A sensor port 42 is formed on side 20 of container 18. A sensor 50 is disposed within sensor port 42 so as to communicate with compartment 28, typically at the lower end thereof. It is appreciate that any number of sensor ports 42 can be formed on container 18 each having a corresponding sensor 50 disposed therein. Examples of sensors 50 that can be used include temperatures probes, pH probes, dissolved oxygen sensors, carbon dioxide sensors, cell mass sensors, nutrient sensors, and any other sensors that allow for testing or checking the culture or production. The sensors can also be in the form of optical sensors and other types of sensors.

Mounted on lower end wall 34 are sparging ports 43 and 44. A first sparger 52 is mounted to port 43 and is designed to deliver small bubbles to culture 29 for oxygenating culture 29. Sparger 52 can be formed integral with or attached to port 43. A second sparger 54 is mounted to port 44 and is designed to deliver larger bubbles to culture 29 for stripping $CO_2$ from culture 29. As such, the bubbles from first sparger 52 are smaller than the bubbles from second sparger 54. In some forms of the invention, second sparger 54 can be an open tube or a tube with a porous frit with relatively large pores, while first sparger 52 can be a tube with a porous frit with relatively small pores. First sparger 52 can also comprise a perforated or porous membrane that is mounted on the end of port 43 or on the interior surface of lower end wall 34 so as to extend over port 43. It is appreciated that spargers come in a variety of different configurations and that any type of spargers can be used as desired or as appropriate for the expected culture volumes, cells and conditions.

It is again noted that container 18 can be formed with any desired number of ports and that the ports can be formed at any desired location on container 18. The ports can be the same configuration or different configurations and can be used for a variety of different purposes such as listed above but not limited thereto. Examples of ports and how various probes, sensors, and lines can be coupled thereto is disclosed in United States Patent Publication No. 2006-0270036, published Nov. 30, 2006 and United States Patent Publication No. 2006-0240546, published Oct. 26, 2006, which are incorporated herein by specific reference in their entirety. The ports can also be used for coupling container 18 to secondary containers, to condenser systems, and to other desired fittings.

Figure 12:
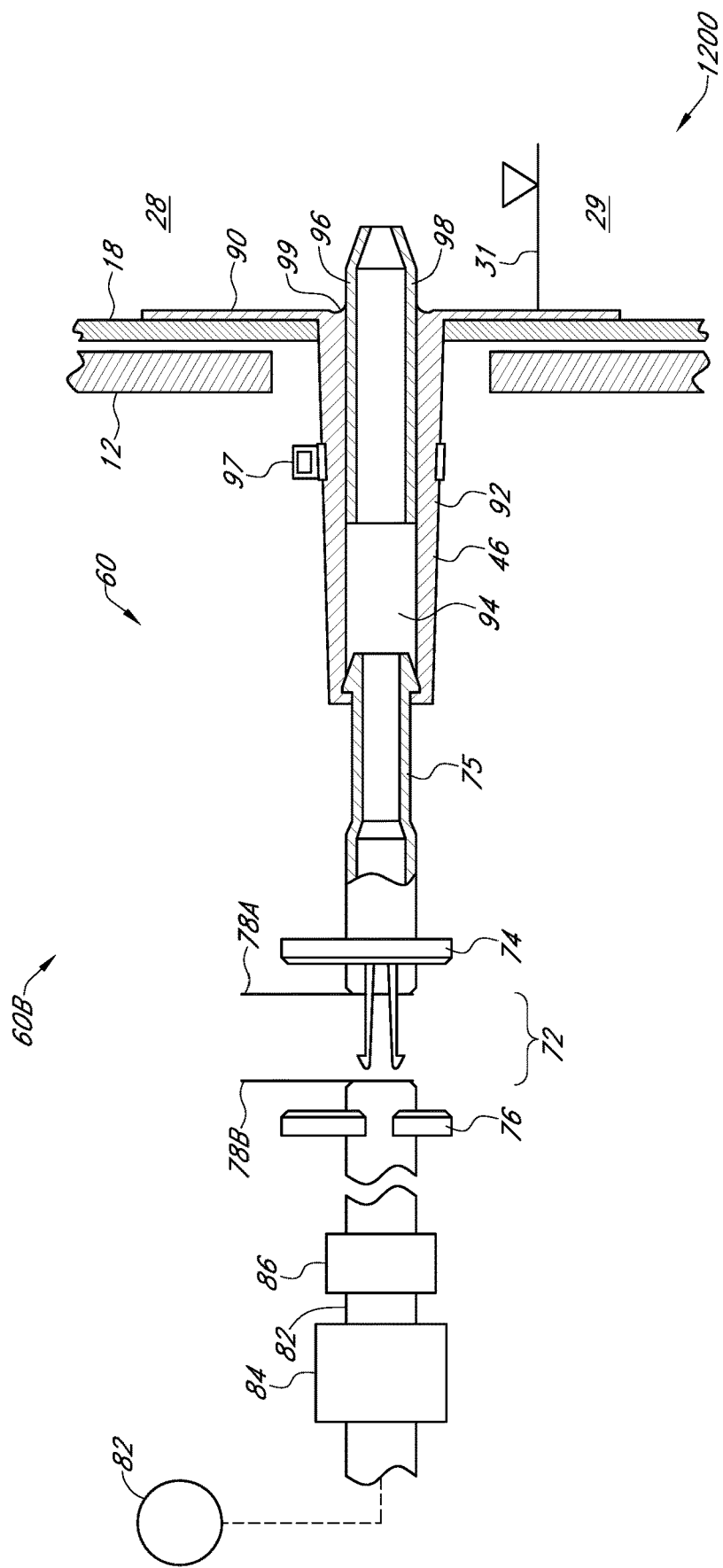
FIG. 12 illustrates a gas delivery system 1200 in accordance with one embodiment.

Also disposed alongside 20 of container 18 are a plurality of vertically spaced apart gas ports 45-47. Each of ports 45-47 forms part of a corresponding gas delivery system, which systems are designed for delivering gas into compartment 28 to produce gas stream oxygenation/mass transfer. Depicted in FIG. 12 is an enlarged view of a gas delivery system 1200, 60A which includes gas port 45. Port 45 comprises a flange 62 mounted to container 18 and a tubular stem 64 outwardly projecting therefrom. Stem 64 bounds a passageway 66 longitudinally extending there through so as to communicate with compartment 28. An annular barb 68 is formed on the free end of stem 64 and couples with a tube 70. In turn, tube 70 couples with an aseptic connector 72.

Aseptic connector 72 includes a first connector portion 74 that selectively mates with and fluid couples to a second connector portion 76. A tubular stem 75 projects from first connector portion 74 and fluid couples with tube 70. Each of connector portions 74 and 76 have a sealing layer 78A and B, respectively, that covers the opening to connector portions 74 and 76. After connector portions 74 and 76 are coupled together, sealing layers 78A and B are pulled out from between the connector portions so as to form an aseptic fluid connection between connector portions 74 and 76. Aseptic connectors are known in the art. One example of an aseptic connector is the KLEENPACK® connector produced by the Pall Corporation. The PALL connector is described in detail in U.S. Pat. No. 6,655,655, the content of which is incorporated herein by reference in its entirety. Other aseptic connectors can also be used.

A tube 80 fluid couples with second connector portion 76 and extends to a gas supply 82. Gas supply 82 delivers a gas which passes through aseptic connector 72, port 45 into compartment 28. The gas can be oxygen or it can be a gas containing oxygen, such as air. Other gases can also be used depending on the desired application. Gas supply 82 can comprise a pressurized canister, a compressor, or other gas supply source. Disposed along tube 80 is a gas filter 84 that sterilizes the gas as it passes there through. Also mounted along tube 80 is a valve 86. Valve 86 is used to selectively stop the flow of gas through delivery system 60A and to prevent culture 29 within container 18 from flowing out through delivery system 60. Valve 86 can have a variety of different configurations. For example, valve 86 can comprise a ball valve, a gate valve, a clamp that pinches tube 80 or any other type of valve that functions for the intended purpose. Valve 86 can be manually controlled or can be electric, hydraulic, pneumatic or the like. It is appreciated that valve 86 can be positioned anywhere along delivery system 60 but is typically located close to gas port 45. In one embodiment, valve 86 can be mounted on tube 70 adjacent to port 45 or directly on port 45.

As previously discussed, the object of gas delivery system 60 is to deliver a stream of gas over top surface 31 of culture 29 or other applicable fluid at a sufficient velocity and direction so that the gas stream produces a turbulence on top surface 31 that is sufficient to oxygenate the culture for growing the cells or microorganisms therein. The term "over" is broadly intended to include the gas traveling over top surface 31 in any desired orientation such as horizontal, substantially horizontal, downwardly inclined, or upwardly inclined. The gas stream need not flow in a linear path but can flow in a circular path or vortex, such as about a vertical or horizontal axis, or can flow along a random path. The gas stream can be a laminar flow or a turbulent flow and the direction, flow rate, and/or speed of the gas flow can be constant or variable. For example, the gas stream can change from a downward vertical direction to a substantially horizontal direction. By placing gas port 64 on side 20 of container 18, the gas passing out through passageway 66 in this embodiment travels horizontally or substantially horizontally within compartment 28 so that it can pass over and across top surface 31. In some embodiments, the gas stream oxygenation can be sufficient to independently oxygenate the culture to the extent needed for growing the cells or microorganisms without any other form of oxygenation, such as sparging. In other embodiments, the gas steam oxygenation can be used in conjunction with sparging or other oxygenation processes.

In one embodiment, the gas stream oxygenation is able to achieve a mass transfer of oxygen using only air and without the aid of sparging having a kLa factor that is greater than 3 and more commonly greater than 5 or 7. The gas stream oxygenation can also maintain, without separate sparging, a stable oxygen concentration set point within the active culture that is in a range of 30%-50% of air saturation. The above values can be achieved in a stirred tank reactor with mixing by impeller and in other types of rectors. In one specific example, gas stream oxygenation, using only air, was able to oxygenate a CHO culture at a target value of 50% of air saturation (868 mbar ambient pressure) and strip $CO_2$ to a cell concentration of 3.5 E+06 cell/mL at $\frac{1}{5}^{th}$ vessel volume. At this point the culture was then fed media to full vessel volume. It is worth noting that the oxygenation and CO2 stripping provided by the gas stream oxygenation was excessive at this level of culture density and vessel fill volume; it required the addition of $N_2$ and $CO_2$ mixed in with the air to hold target pH and dissolved $O_2$ target values.

During operation, compartment 28 of container 18 is filled with culture 29 so that top surface 31 is disposed close to passageway 66. In one embodiment, the distance $D_1$ between passageway 66 and top surface 31 is in a range between about 0.75 cm to about 15 cm with about 1 cm to about 10 cm or about 2 cm to about 5 cm being more common. Other distances can also be used. Furthermore the distance $D_1$ can vary based upon factors such as the size of container 18, the projection angle of the gas (with flow perpendicular to the liquid surface being optimal), the flow rate of the gas, and the superficial velocity of the gas. When measuring the distance $D_1$, top surface 31 can be the maximum liquid wave height under agitation of culture 29 or can be top surface 31 with no agitation. For scalable representation, the flow rate can be measured in rate of Vessel Volumes per Minute (VVM) of the maximum rated liquid working volume of the system. The flow rate of the gas passing out through passageway 66 is typically in a range between about 0.06 VVM to about 0.2 VVM with about 0.08 VVM to about 0.1 VVM or about 0.16 VVM to about 0.18 VVM being more common. Other flow rates can also be used depending on the intended application. The velocity of the gas exiting passageway 66 or traveling across top surface 31 within compartment 28 is typically in a range between about 25 m/sec to about 275 m/sec with about 25 m/sec to about 175 m/sec or about 30 m/sec to about 100 m/sec being more common. The velocity can be greater than 25 m/sec and more commonly greater than 40 m/sec, 60 m/sec, 80 m/sec, or 100 m/sec. To achieve desired gas velocities exiting passageway 66, passageway 66 can have a minimum exit area of flux based on the volume of compartment 12, i.e., vessel volume (VV). This minimum exit area of flux can be in a range between about VV (liters)/80 (liters/mm$^2$) to about VV (liters)/7.8 (liters/mm$^2$) with about VV (liters)/40 (liters/mm$^2$) to about VV (liters)/30 (liters/mm$^2$) or about VV (liters)/8.5 (liters/mm$^2$) to about VV (liters)/6.25 (liters/mm$^2$) being more common. Other areas can also be used.

If desired, port 45 can be configured so that during operation stem 64 is angled so that the gas passing out therethrough is directed slightly down towards top surface 31. For example, stem 64 has a central longitudinal axis 88. Port 45 can be formed so that axis 88 of stem 64 is tilted relative to horizontal during use by an angle α in a range between 1° to about 10° so that the gas passing out therethrough passes slightly down against top surface 31. Other angles can also be used.

As previously discussed, gas stream oxygenation is most efficient for shallow depths of culture 29 within container 18. In one embodiment, the maximum distance $D_2$ (See FIG. 11) between top surface 31 and lower end wall 34 at which the gas stream oxygenation can independently oxygenate culture 29 to grow cells or microorganisms can be in a range of distances based on diameter of the container 18, i.e., vessel diameter (VD). For example, maximum distance $D_2$ can be in a range between about VD (cm)*0.3 to about VD (cm)*0.4. Where container 18 does not have a circular transverse cross section, VD can be based on an average diameter. In some specific examples, $D_2$ can be in a range between about 5 cm to 30 cm or between 10 cm and 100 cm depending on the diameter of the container. Other distances can also be used. At some depths, the system can operate without the use of sparging or other oxygenation systems. In addition, for some depths desired oxygenation can be achieved throughout the culture without the use of a separate mixer due to the natural circulation caused by the blowing gas. As the depth increases, however, proper oxygenation of the culture requires both gas steam oxygenation and a separate mixing system, such as thorough an impeller or rocking, to ensure all of the culture is properly oxygenated.

As the depth of culture 29 increases, sensors 50 may detect the need for additional oxygenation, even when mixing is being accomplished. An electrical controller or manual regulator can then be used to regulate the flow of sparged gas through spargers 52 and 54 for further controlling the oxygenation and $CO_2$ levels within culture 29. Although sparging with air or oxygen may not be required at shallow depths when using gas steam oxygenation, sparging with nitrogen, such as through sparger 54, may still be used at all depths to control the oxygen within the culture, i.e., to strip out excess oxygen produced by gas steam oxygenation. Although gas delivery system 60A is shown in FIG. 11 as the only gas delivery system that is located at or near the elevation on container 18 corresponding to the top of distance $D_2$, two or more gas delivery systems 60A can be located and simultaneously operated at or near that same elevation.

The gas delivered to container 18 through gas delivery system 60A can be drawn out through access port 41 so that container 18 does not over inflate. Because of the rather high volume of gas passing through container 18, there can be a higher rate of evaporation of the media relative to conventional systems. As such, reactor system 10 can be operated with a condenser that couples with access port 41. One example of a condenser that can be used with reactor system 10 is disclosed in US Patent Publication No. 2011/0207218 A1, published Aug. 25, 2011, which is incorporated herein by specific reference in its entirety.

Culture 29 continues to grow at a level below passage 66 until a defined mass density or other desired value is determined within culture 29. Valve 86 can then be closed and media and other components added to culture 29 until the level of top surface 31 is raised to within an operating distance from a second gas delivery system 60B shown in FIG. 11. Gas delivery system 60B is then activated to again pass a gas stream over top surface 31 and thereby continue with the gas stream oxygenation of culture 29. This process can then be continued for a subsequent gas delivery system 60C. Likewise, any number of additional gas delivery systems can be vertically spaced apart alongside 20 of container 18 for continuing gas stream oxygenation at other elevations.

Figure 13:
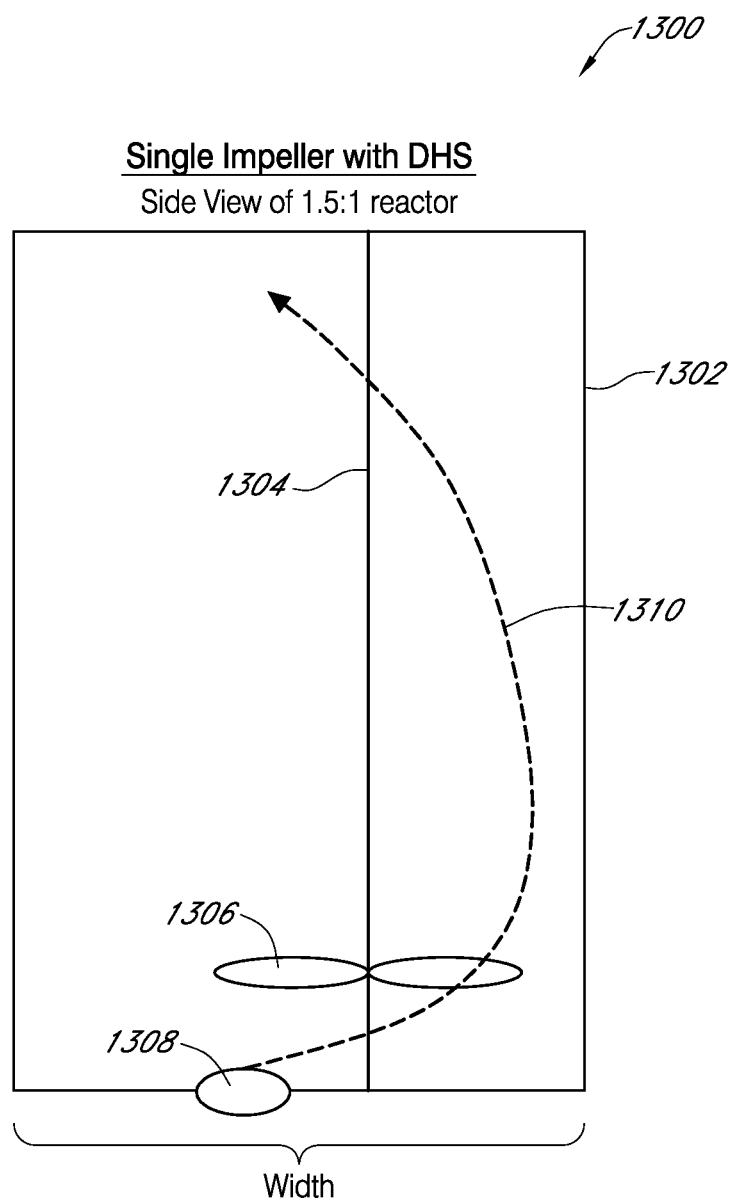
FIG. 13 illustrates a mixing system 1300 showing gas bubble trajectory according a single impeller embodiment.

FIG. 13 illustrates a fluid mixing system 1300 according to various embodiments. In various embodiments the mixing system 1300 may comprise a compartment 1302 having a drive shaft 1304 with an impeller 1306 and a sparger 1308 with a gas bubble path 1310 showing the trajectory of gas bubbles rising out of the sparger 1308.

In various embodiments, the compartment 1302 includes an aspect ratio of 1.5 and sparger 1308 is positioned relative to a single impeller 1306 in a position that is suboptimal for gas bubble re-entrainment. Various application may require that bubbles are not re-entrained, but more frequently re-entrainment leads to increased gas bubble residence time in the mixing system 1300 which is preferred most of the time.

Figure 14:
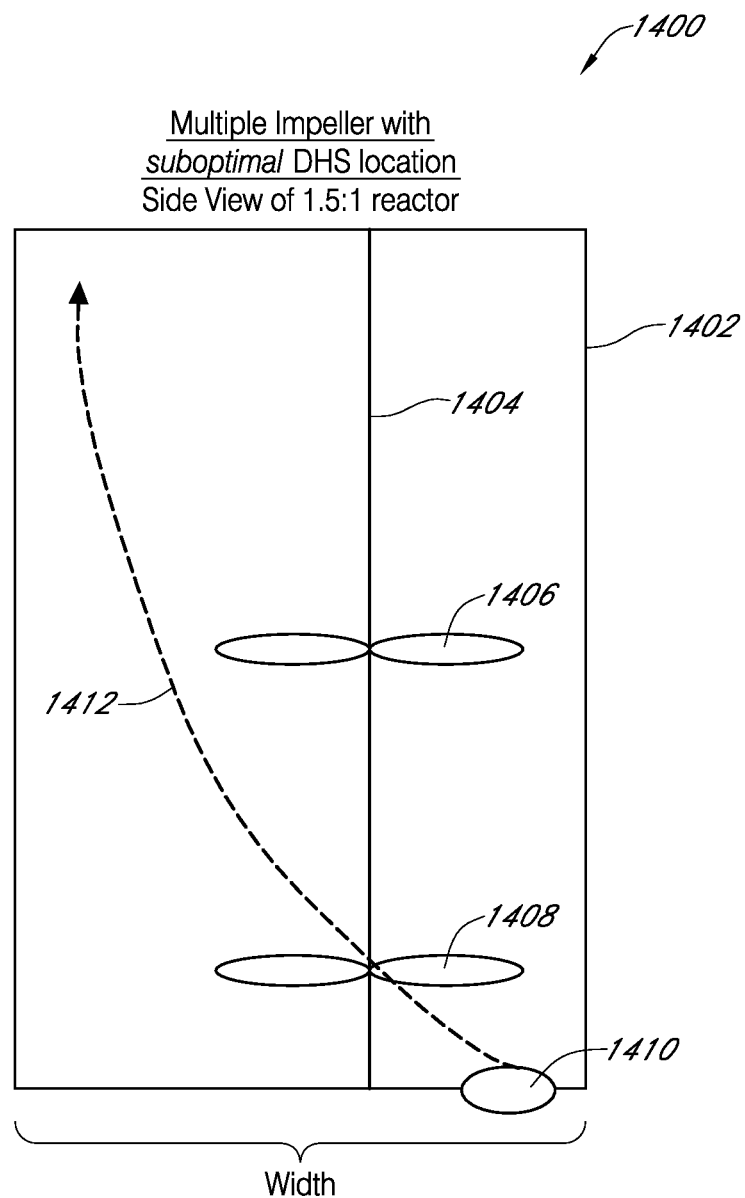
FIG. 14 illustrates a mixing system 1400 showing gas bubble trajectory having a suboptimally placed sparger.

FIG. 14 illustrates a fluid mixing system 1400 according to various embodiments. In various embodiments the mixing system 1400 may comprise a compartment 1402 with a drive shaft 1404 disposed therein, affixed to the drive shaft 1404 a second impeller 1406 and a first impeller 1408 and a sparger 1410 affixed to the bottom of the compartment 1402 with a gas bubble path 1412 extending therefrom.

In various embodiments, the sparger 1410 location relative to the drive shaft 1404 and first and second impeller 1406, 1408 locations is suboptimal for gas bubble re-entrainment. Such a system is sometimes preferred when additional mixing is required and there is no need to increase bubble residence times. However, in most applications the relative locations of the sparger 1410 and impellers 1406, 1408 can be selected to alter the gas bubble path 1412 and cause longer residence times for the bubbles.

Figure 15:
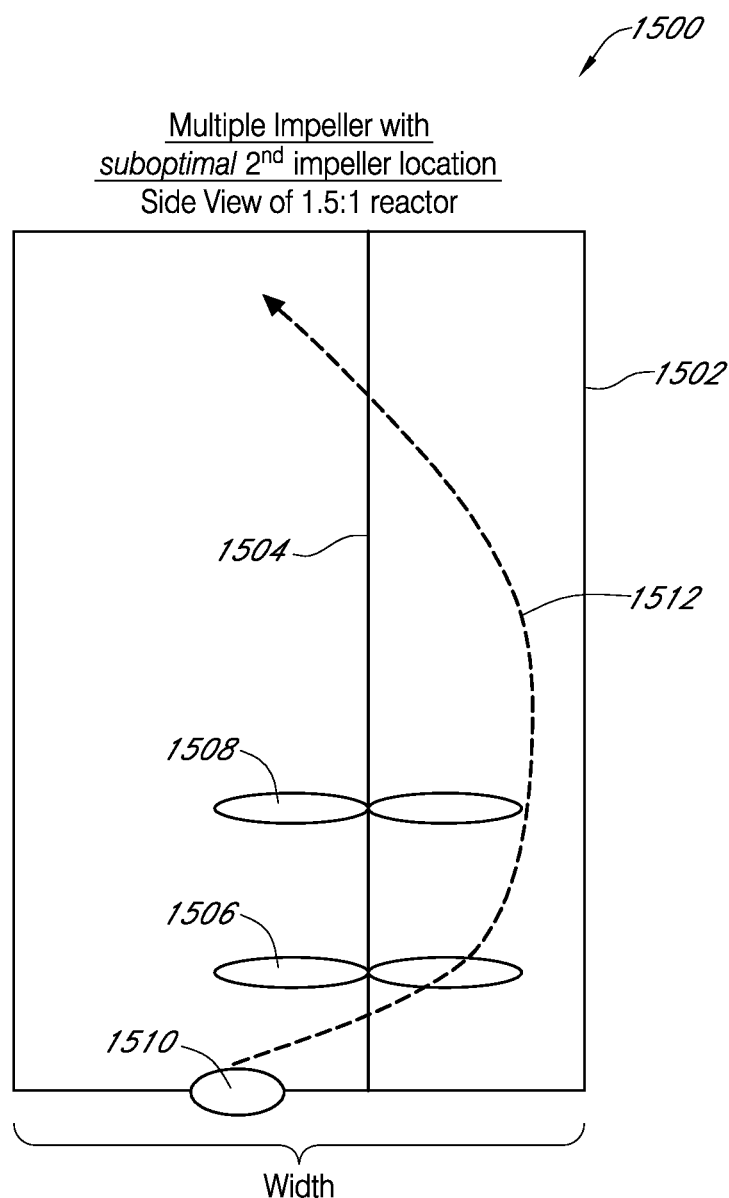
FIG. 15 illustrates a mixing system 1500 showing gas bubble trajectory having a suboptimally placed second impeller.

FIG. 15 illustrates a fluid mixing system 1400 according to various embodiment. In various embodiments, the mixing system 1500 may comprise a compartment 1502, a drive shaft 1504 disposed within the compartment, a first impeller 1506 and a second impeller 1508 affixed to the drive shaft 1404, a sparger 1510, and a gas bubble path 1512.

In various embodiments, the relative locations of the sparger 1510 and first and second impellers 1506, 1508 are suboptimal for gas bubble re-entrainment. There are some applications where shorter gas bubble residence times are optimal, but in the majority of situations this is not a desirable configuration.

Figure 16:
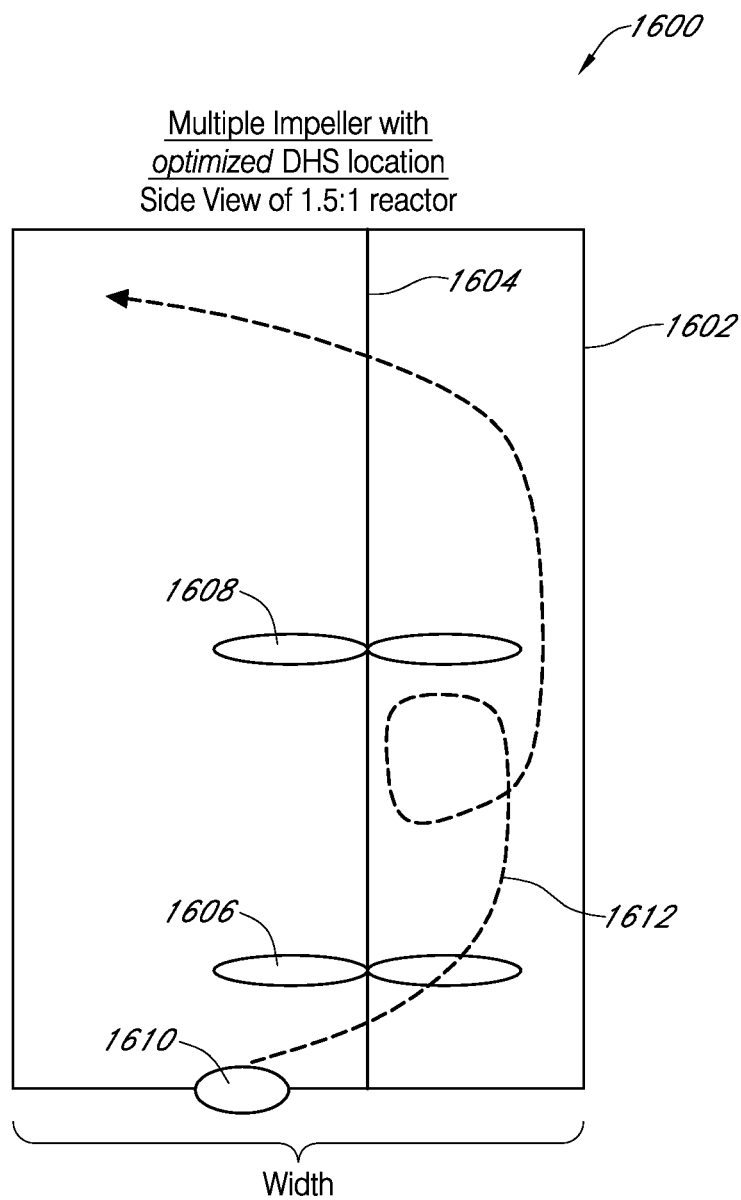
FIG. 16 illustrates a mixing system 1600 showing gas bubble trajectory having an optimally placed sparger and set of impellers.

FIG. 16 illustrates a fluid mixing system 1600 according to various embodiments. In various embodiments, the mixing system 1600 may comprise a compartment 1602, a drive shaft 1604 disposed within the compartment 1402, a first impeller 1606 and a second impeller 1608 affixed to the drive shaft 1404, a sparger 1610, and a gas bubble path 1612 depicting the rising flow of gas bubbles originating from the sparger 1410.

In various embodiments, the fluid mixing system 1600 of FIG. 16 is optimized for re-entrainment. The relative positions of the sparger 1410 and first and second impellers 1606, 1608 were selected to influence the gas bubble path 1612, thereby, increasing bubble residence time within the mixing system 1600. In the majority of applications, this is an ideal arrangement.

Figure 17:
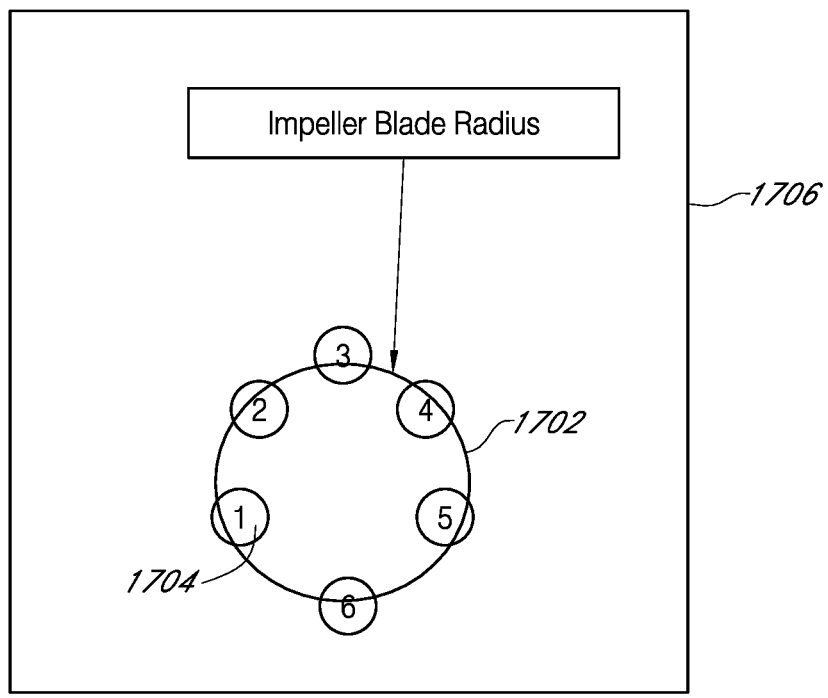
FIG. 17 illustrates a sparger layout 1700 in accordance with one embodiment.
Figure 18A:
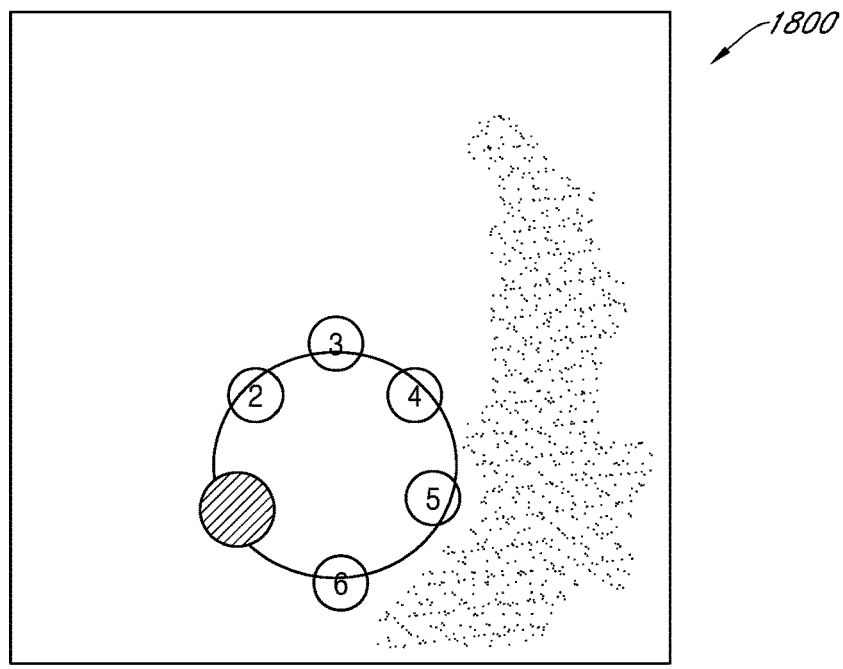
FIGS. 18A-F illustrate a gas distribution pattern using different sparger locations in accordance with one embodiment.
Figure 18B:
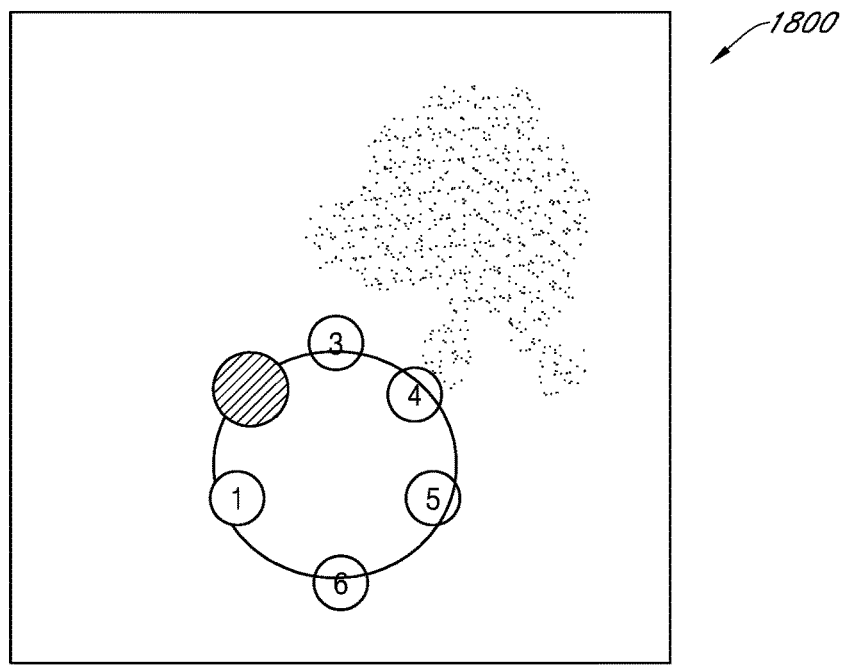
Figure 18C:
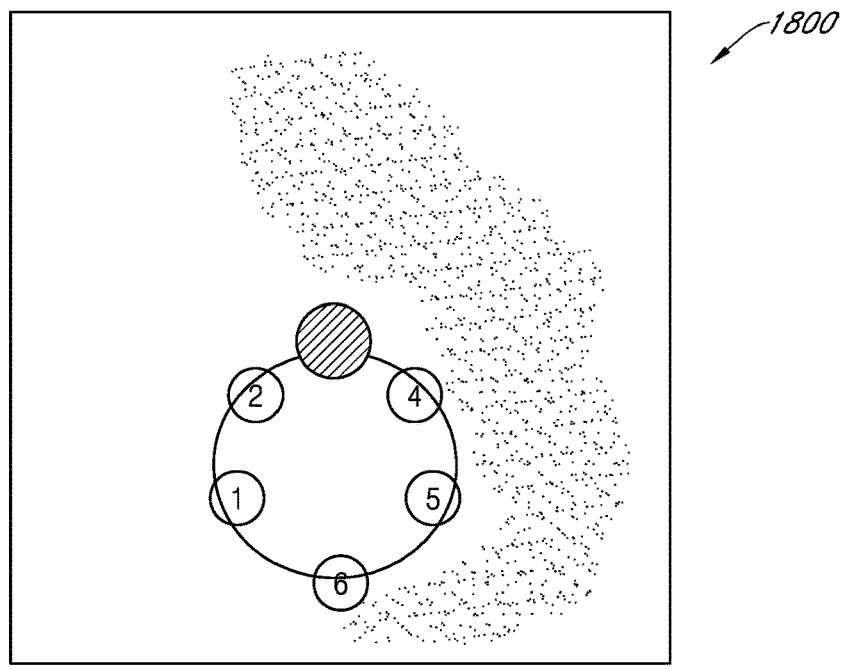
Figure 18D:
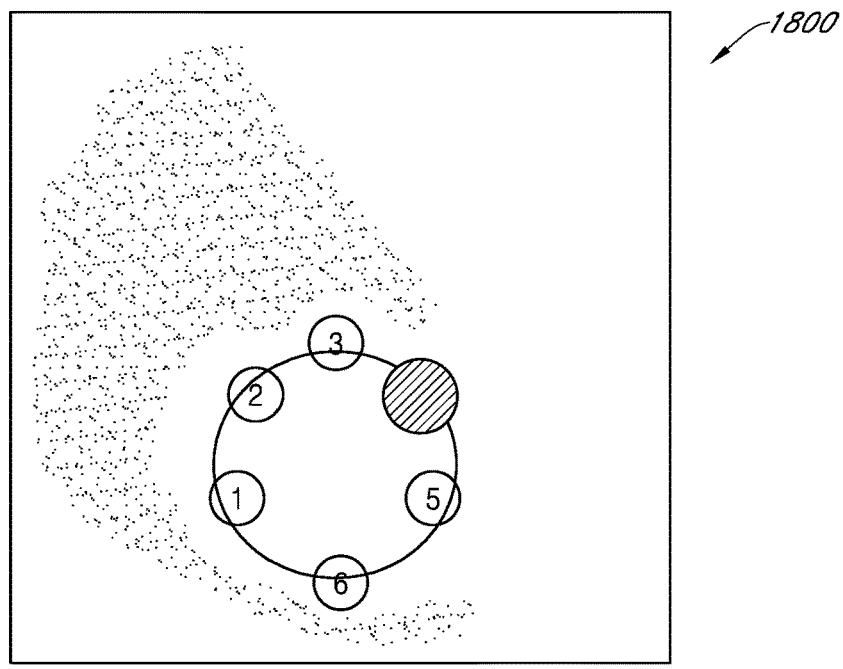
Figure 18E:
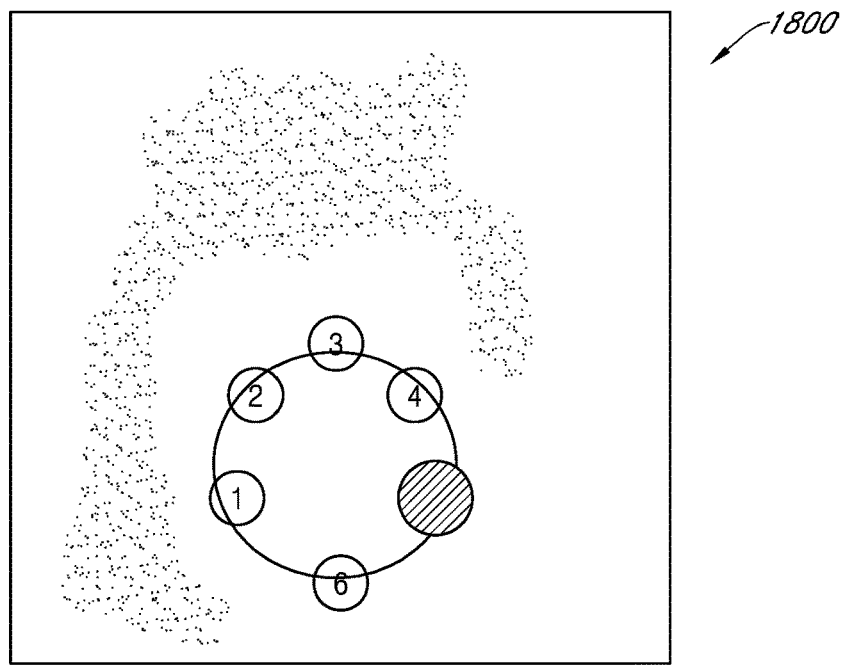
Figure 18F:
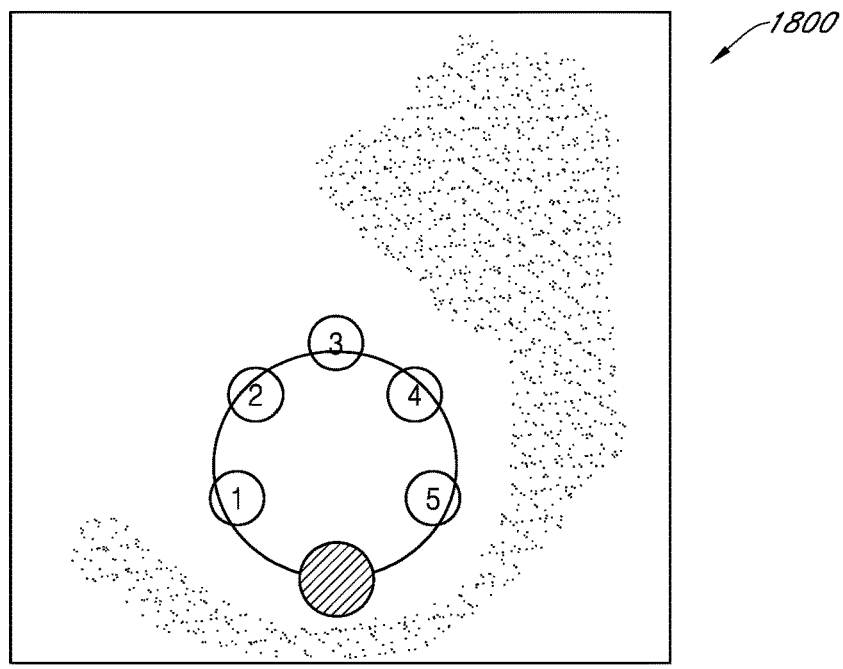

FIG. 17 illustrates a sparger layout 1700 for experimental purposes. The sparger layout 1700 comprises an impeller tip sweep 1702, sparger positions 1704, and a compartment 1706.

FIG. 17 sets up an experiment where a drive shaft (not shown) is offset toward the sidewall of a compartment 1706 and various sparger positions 1704 were operated one at a time to determine optimal gas bubble dispersal patterns. In various embodiments, the corners of the compartment 1706 act to increase gas bubble distribution by acting as baffles.

FIGS. 18A-18F illustrate the gas bubble distribution patterns for each of the sparger positions 1704 shown in FIG. 17. The grayed out sparger position indicates which sparger is in operation. The other spargers are turned off. For example, sparger position 1 is in operation in FIG. 18A while the other sparger positions are turned off.

Figure 19:
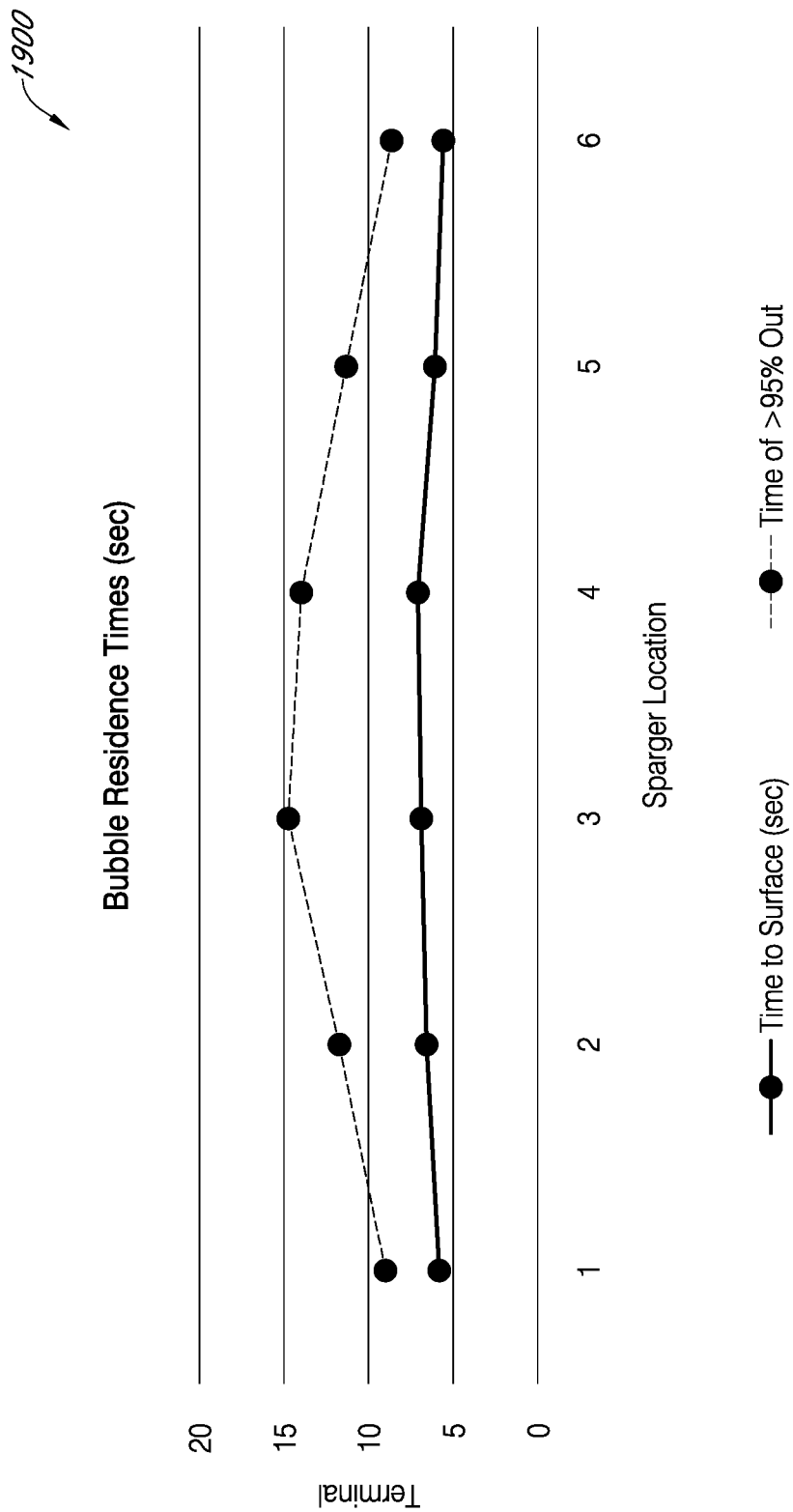
FIG. 19 illustrates gas bubble residence times 1900 from gas arising out of various sparger locations in accordance with one embodiment.

FIG. 19 illustrates the performance of the sparger positions 1704 shown in FIG. 17. The x-axis indicates the sparger positions 1704 in use and the y-axis shows the time elapsed. The solid line shows the time in seconds it takes for the first released bubbles to reach the surface and the dashed line shows the time is takes for 95% of bubbles to come to the surface after gas flow to the sparger has ceased. Generally, having bubbles stay in the fluid longer means that more dissolved oxygen can go into the fluid and nurture the cells which is preferred for most applications. When creating a scalable system increasing or decreasing the bubble residence time to match kLa between two or more mixing systems will allow for better predictive models of commercial scale production. As discussed previously, being able to alter the sparger and impeller locations to change re-entrainment properties can be helpful.

Figure 20:
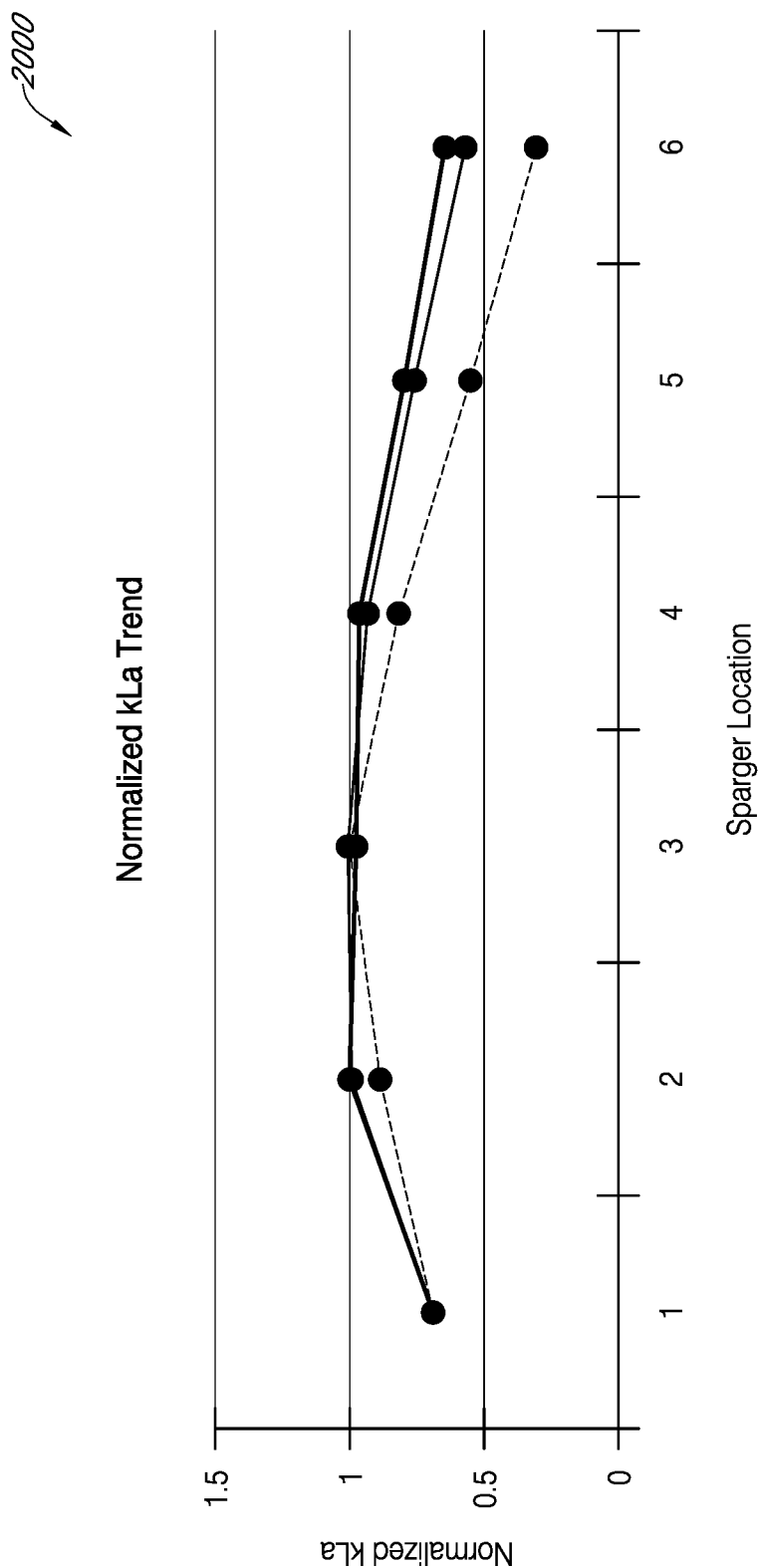
FIG. 20 illustrates a kLa trend 2000 using various sparger locations in accordance with one embodiment.

FIG. 20 illustrates the performance of the sparger positions 1704 shown in FIG. 17. The x-axis indicates the sparger positions 1704 in use and the y-axis shows the normalized kLa values obtained. Generally, a higher kLa value is preferable. In a scalable system, sparger locations can be selected to attempt to match kLa values between two or more mixing systems having different geometries and volumes.

Figure 21:
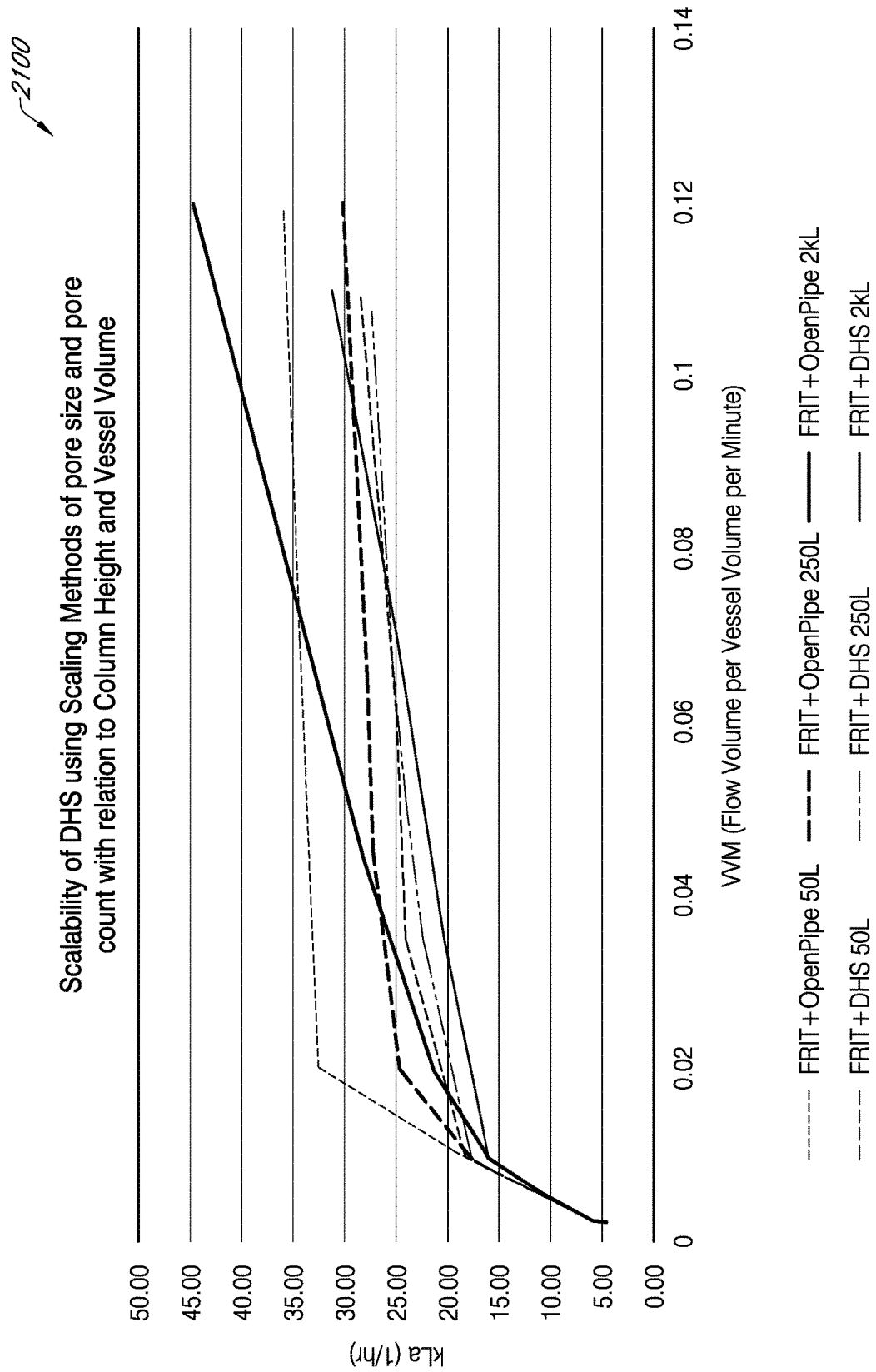
FIG. 21 illustrates a sparger performance 2100 in accordance a variety embodiments.

FIG. 21 illustrates comparison data across mixing system volumes using the sparging methods and systems described in this application versus prior art sparging systems. kLa is depicted on the y-axis and flow volume per vessel volume per minute is depicted on the x-axis. It is clearly shown that prior art sparging systems and methods do not produce similar kLa values between 50 liter to 2000 liter systems. However, spargers disclosed herein produce quite similar kLa values between systems having different volumes.

Using methods described above, sparger pore size and count were scaled and kLa was empirically measured comparing systems with FRIT+open pipe to systems with FRIT+DHS (sparger system and method disclosed above).

Across scales, this method improves scaled performance, reducing maximum standard deviations of kLa across scales from 20% to 8.6% and reducing average standard deviation of kLa across scales employing open-pipe or DHS from 16% to 6%.

Figure 22:
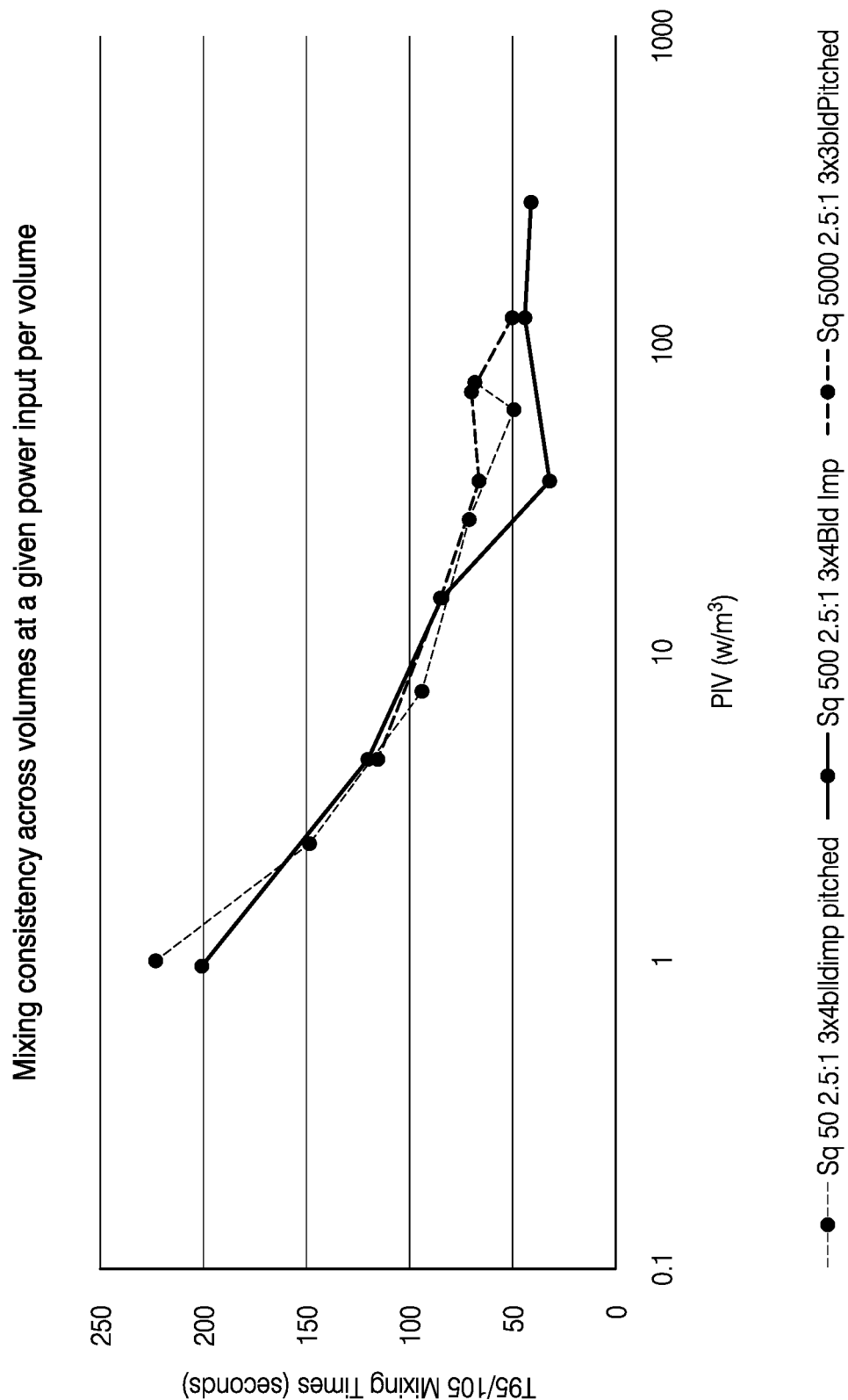
FIG. 22 illustrates a mixing consistency 2200 across volumetric scales.

FIG. 22 illustrates mixing consistency across volumes at a given power input per volume. The mixing system 200 used to produce the data seen in FIG. 22 is that depicted in FIG. 2 and elsewhere in this document. The plots shown are from data taken from a 50 liter vessel having a 2.5 aspect ratio and 3 impellers, a 500 liter vessel having a 2.5 aspect ratio and 3 impeller, and a 5000 liter vessel having a 2.5 aspect ratio and 3 impellers. The impeller diameters were not the same across each scale nor the impeller diameter to vessel width ratios. As can be seen, the t95 mixing times remain constant across scales at a given power per volume.

FIG. 23 illustrates a table showing at or near constant impeller tip speeds and power per volume across scales 50, 100, 250, 500, 1000, and 2000 liter systems. The diameter and number of impellers has changed to accommodate different sized systems.

Figure 24:
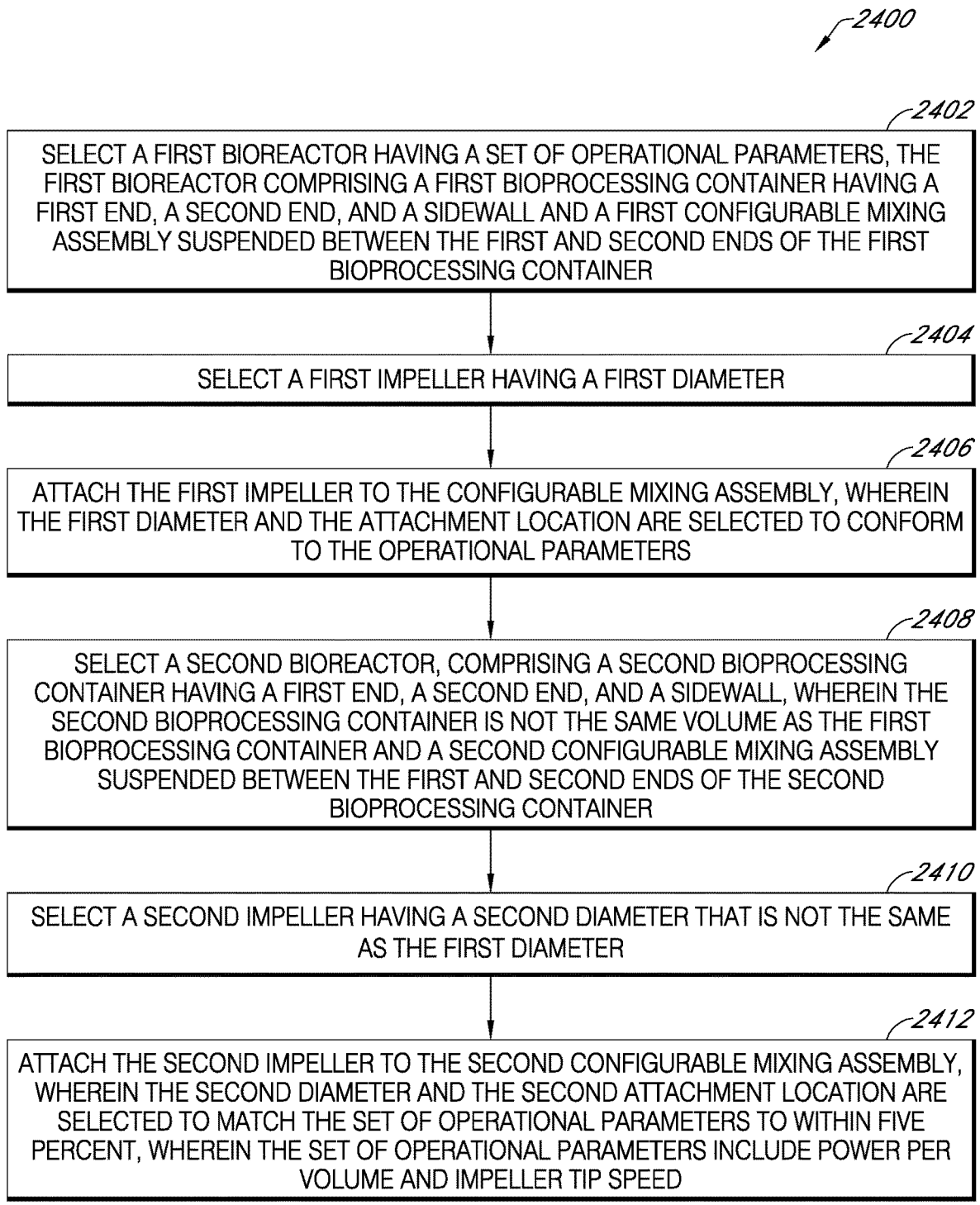
FIG. 24 illustrates a method of matching fluid mixing characteristics between bioreactors having different volumes.

FIG. 24 illustrates a method of matching fluid mixing characteristics between bioreactors having different volumes 2400 according to various embodiments. Block 2402 includes the step of selecting a first bioreactor having a set of operational parameters, the first bioreactor comprising a first bioprocessing container having a first end, a second end, and a sidewall and a first configurable mixing assembly suspended between the first and seconds ends of the first bioprocessing container. Block 2404 includes the step of selecting a first impeller having a first diameter. Block 2406 includes the step of attaching the first impeller to the configurable mixing assembly, wherein the first diameter and the attachment location are selected to conform to the operational parameters. Block 2408 includes the step of selecting a second bioreactor, comprising a second bioprocessing container having a first end, a second end, and a sidewall, wherein the second bioprocessing container is not the same volume as the first bioprocessing container and a second configurable mixing assembly suspended between the first and second ends of the second bioprocessing container. Bloc 2410 includes the step of selecting a second impeller having a second diameter that is not the same as the first diameter. Block 2412 includes the step of attaching the second impeller to the second configurable mixing assembly, wherein the second diameter and the second attachment location are selected to match the set of operational parameters to within five percent, wherein the set of operational parameters include power per volume and impeller tip speed.

Figure 25:
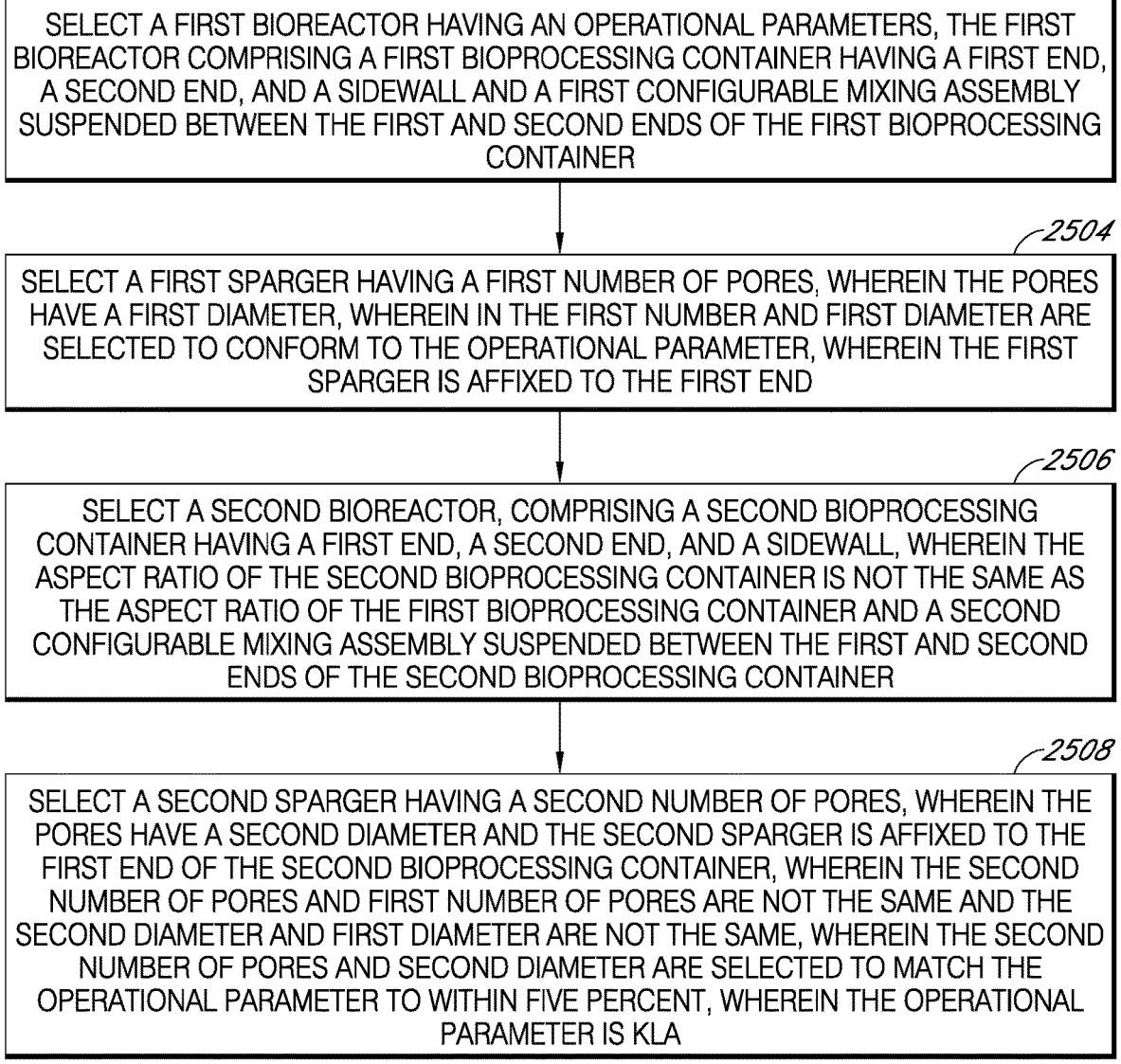
FIG. 25 illustrates a method of match fluid mixing characteristics between bioreactors having different volumes.

FIG. 25 illustrates a method of matching fluid mixing characteristics between bioreactors having different volumes 2500 according to various embodiments. Block 2502 includes the step of selecting a first bioreactor having an operational parameters, the first bioreactor comprising a first bioprocessing container having a first end, a second end, and a sidewall and a first configurable mixing assembly suspended between the first and seconds ends of the first bioprocessing container. Block 2504 includes the step of selecting a first sparger having a first number of pores, wherein the pores have a first diameter, wherein in the first number and first diameter are selected to conform to the operational parameter, wherein the first sparger is affixed to the first end. Block 2506 includes the step of selecting a second bioreactor, comprising a second bioprocessing container having a first end, a second end, and a sidewall, wherein the aspect ratio of the second bioprocessing container is not the same as the aspect ratio of the first bioprocessing container and a second configurable mixing assembly suspended between the first and second ends of the second bioprocessing container. Block 2508 includes the step of selecting a second sparger having a second number of pores, wherein the pores have a second diameter and the second sparger is affixed to the first end of the second bioprocessing container, wherein the second number of pores and first number of pores are not the same and the second diameter and first diameter are not the same, wherein the second number of pores and second diameter are selected to match the operational parameter to within five percent, wherein the operational parameter is kLa.

Figure 26:
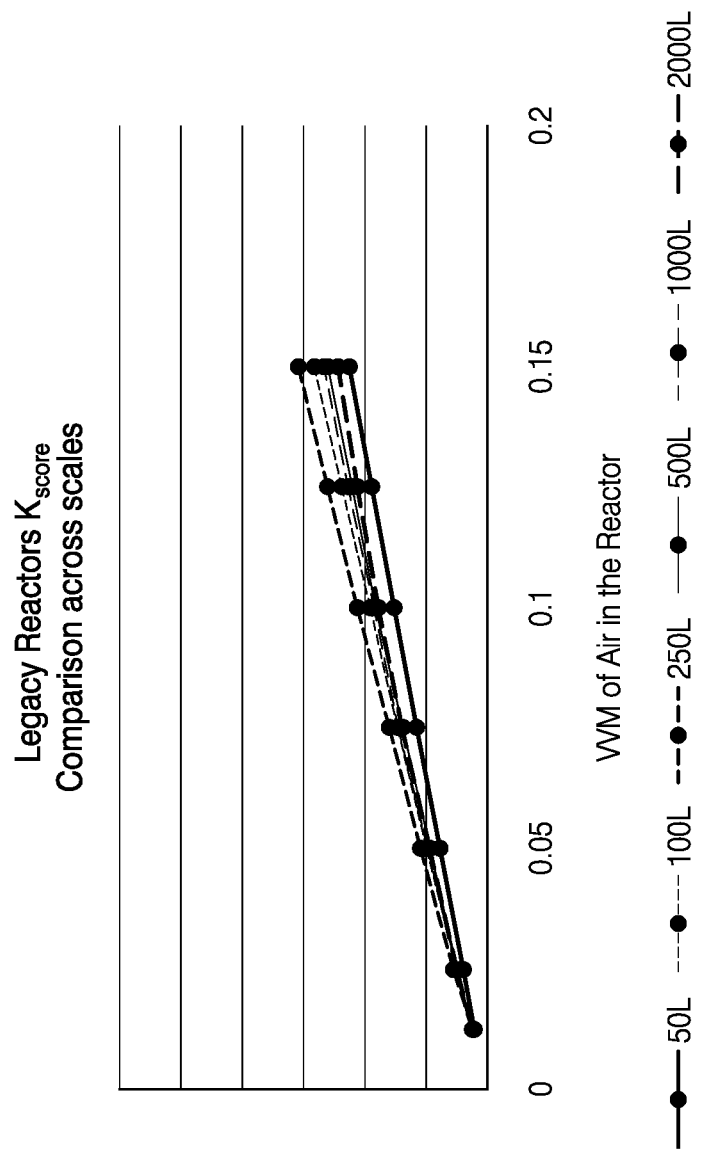
FIG. 26 illustrates Kscore comparisons between legacy bioreactors having different volumes.
Figure 27:
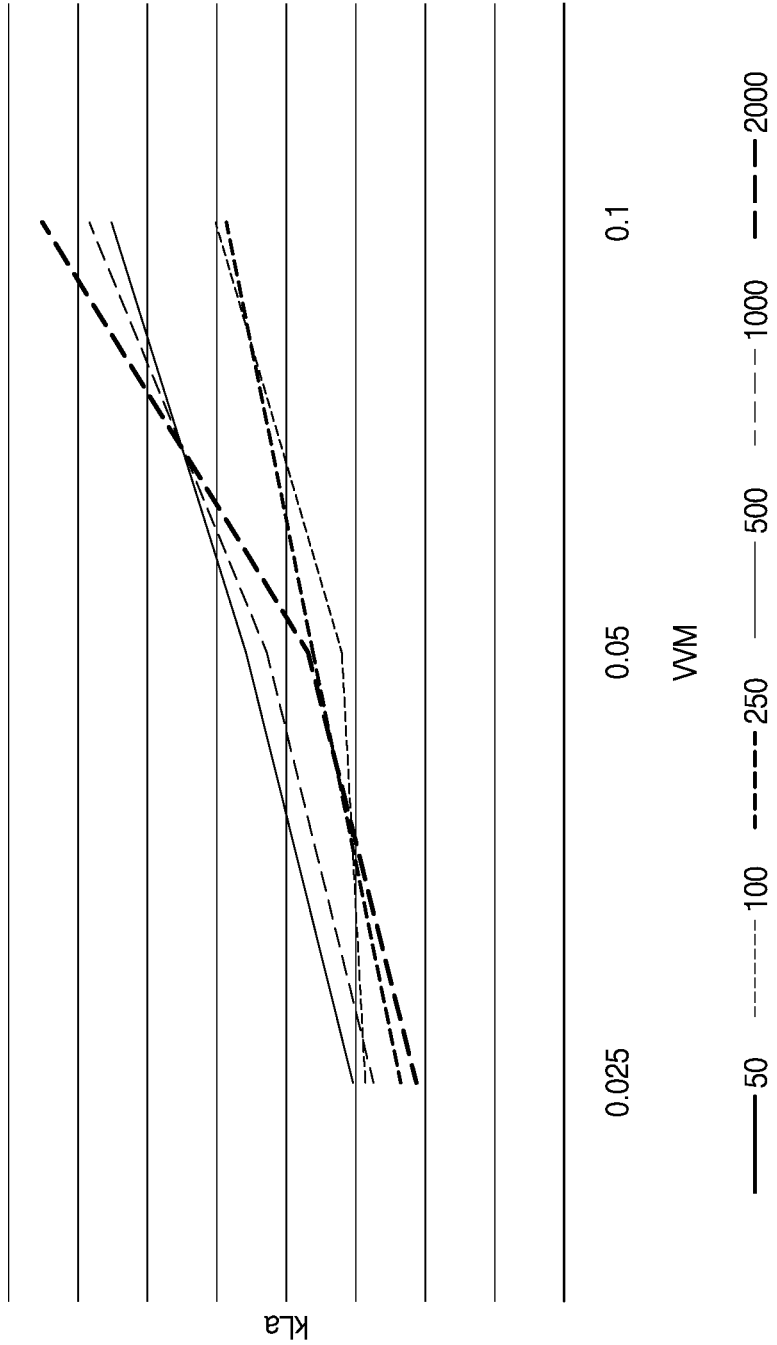
FIG. 27 illustrates kLa comparison data across scales.
Figure 28:
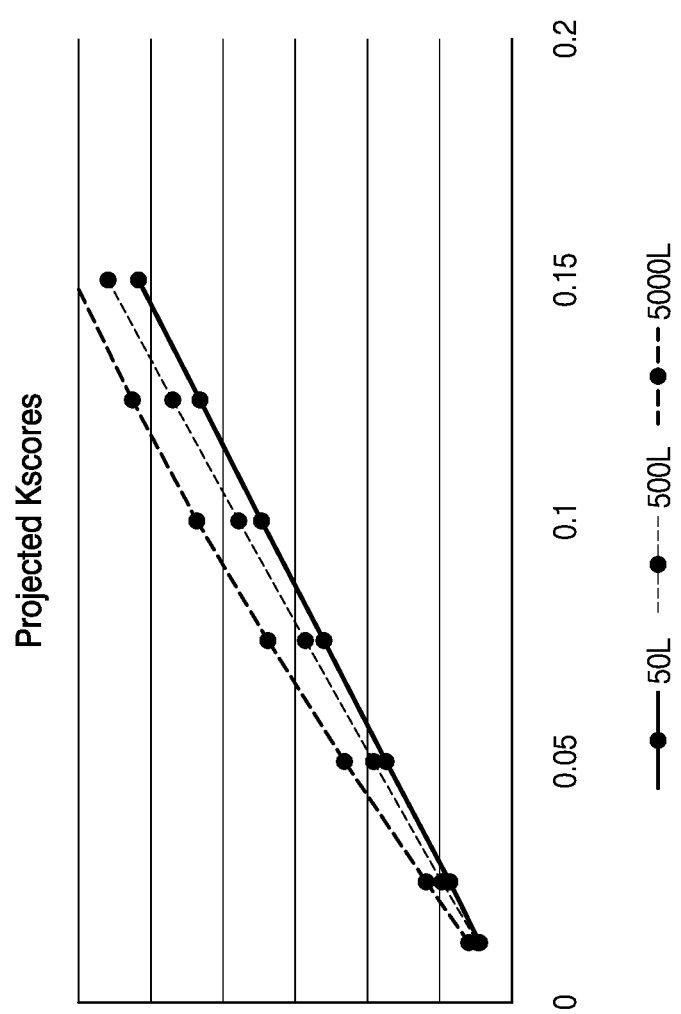
FIG. 28 illustrates projected Kscores between scales in the system described herein.

A series of predictive and actual data were collected and presented in FIGS. 26, 27, and 28. The following is a way to predict the required pore size to ensure scaling across bioreactors having different volumes.

1. Using empirical data and literature-based regression, predict
   a. Bubble Size from pore size and flow rate (internal empirical data regression)
   b. Bubble terminal Velocity (Talaia, 2007, Terminal velocity of a bubble rise in liquid column, also validated through measurements of bubble velocities in house).
   c. Residence time based on liquid column height divided by bubble terminal velocity
2. kLa Score is based on:

$$K_{Score} = \frac{SurfaceArea_{Single\_bubble} \times \#Bubbles_{per\ second} \times ResidenceTime}{VesselVolume} \ [=]$$

units of $cm^2/L$

FIG. 26 illustrates predictive Kscore comparison data across scales on legacy bioreactors.

FIG. 27 illustrates actual kLa comparison data across scales on legacy bioreactors.

FIG. 28 illustrates projected Kscore comparison data across scales on some of the embodiments disclosed herein.

Using the systems and methods disclosed herein, operational parameters can be kept constant across mixing systems accommodating different volumes. When moving from a test or bench scale to a commercial scale the most import aspect is to be able to easily predict growth conditions for a bioreactor. The scalable system herein allows a user to create such a system by adjusting various aspects of the sparger design, drive system, and headspace airflow system where the components across systems may be completely different, but produce the same or similar results. It should be noted that all the systems interact with one another and when selections are made the other aspects need to be considered. For example, if bubble residence time needs to be increased the drive system can altered to re-entrain bubbles. If CO2 build up needs to be reduced then additional sparging and airflow across the headspace may be increased. Until now a user needed to decide what metric was more important (shear, power per volume, or kLa) and design scalable systems that were the same dimensionally (vessel aspect ratio, impeller diameter to vessel width/diameter, etc.). With the presently disclosed invention, various operational parameters can be kept constant with the understanding of how various systems influence one another.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art will readily appreciate that the sequences may be varied and still remain within the spirit and scope of the various embodiments.

What is claimed is:

1. A method of matching fluid mixing characteristics between bioreactors having different volumes, comprising:
   selecting a first bioreactor having a set of operational parameters, the first bioreactor comprising:
      a first bioprocessing container having a first end, a second end, and a sidewall; and
      a first configurable mixing assembly suspended between the first and second ends of the first bioprocessing container;
   selecting a first impeller having a first diameter;
   attaching the first impeller to the first configurable mixing assembly, wherein the first diameter and a first attachment location are selected to conform to the set of operational parameters;
   selecting a first sparger, wherein the first sparger is affixed to the first end of the first bioprocessing container at a first position selected to conform to the set of operational parameters;
   selecting a second bioreactor, comprising:
      a second bioprocessing container having a first end, a second end, and a sidewall, wherein a volume of the second bioprocessing container is not the same as a volume of the first bioprocessing container; and
      a second configurable mixing assembly suspended between the first and second ends of the second bioproces sing container;
   selecting a second impeller having a second diameter that is not the same as the first diameter;
   attaching the second impeller to the second configurable mixing assembly, wherein the second diameter and a second attachment location are selected to match the set of operational parameters;
   selecting a second sparger, wherein the second sparger is affixed to the second end of the second bioprocessing container at a second position that is not the same as the first position, the second position being selected to match the set of operational parameters;
   wherein the set of operational parameters includes power per volume and impeller tip speed.

2. The method of claim 1, further comprising the step of selecting a third impeller having a third diameter that is not the same as the first diameter and attaching the third impeller to the second configurable mixing assembly, wherein the third diameter and a third attachment location are selected in combination with the second diameter and the second attachment location to match the set of operational parameters.

3. The method of claim 2, wherein the step of adding the third impeller reduces second and third impeller tip speeds required to match the set of operational parameters.

4. The method of claim 1, wherein a ratio of the first impeller diameter to a width of the first bioprocessing container is not the same as a ratio of the second impeller diameter to a width of the second bioprocessing container.

5. The method of claim 1, wherein the set of operational parameters further includes bulk fluid flow and T95 mixing times.

6. The method of claim 5, wherein the set of operational parameters is selected based on optimal growth conditions for a cell.

7. The method of claim 6, wherein the cell is eukaryotic and sensitive to a shear that increases as the impeller tip speed increases.

8. The method of claim 1, wherein the first bioprocessing container is of a bench scale volume between 0.1 liters and 50 liters and the second bioprocessing container is of a commercial volume between 50 liters and 10,000 liters.

9. The method of claim 8, wherein the first and second bioprocessing containers are rectangular in shape and the first and second configurable mixing assemblies are offset from a center axis to increase bulk fluid flow.

10. The method of claim 9, wherein an aspect ratio of the first and second bioprocessing containers is greater than 1.5.

11. A method of matching fluid mixing characteristics between bioreactors having different volumes, comprising:
    selecting a first bioreactor having an operational parameter, the first bioreactor comprising:
        a first bioprocessing container having a first end, a second end, and a sidewall; and
        a first configurable mixing assembly suspended between the first and second ends of the first bioprocessing container;
    selecting a first sparger having a first number of pores, wherein the pores have a first diameter, wherein the first number and first diameter are selected to conform to the operational parameter, wherein the first sparger is affixed to the first end;
    attaching a first impeller to the first configurable mixing assembly, the first sparger and first impeller having a first position selected to conform to the operational parameter and the first impeller configured to re-entrain gas bubbles rising out of the first sparger;
    selecting a second bioreactor, comprising:
        a second bioprocessing container having a first end, a second end, and a sidewall, wherein an aspect ratio of the second bioprocessing container is not the same as an aspect ratio of the first bioprocesing container; and
        a second configurable mixing assembly suspended between the first and second ends of the second bioprocesing container;
    selecting a second sparger having a second number of pores, wherein the pores have a second diameter and the second sparger is affixed to the first end of the second bioprocessing container,
    attaching a second impeller to the second configurable mixing assembly, the second sparger and second impeller having a second position and the second impeller configured to re-entrain gas bubbles rising out of the second sparger;
    wherein the second number of pores and first number of pores are not the same and the second diameter and first diameter are not the same,
    wherein the first position is not the same as the second position,
    wherein the second number of pores and second diameter in combination with the second position of the second sparger and second impeller are selected to match the operational parameter to within five percent, wherein the operational parameter is kLa.

12. The method of claim 11, wherein the first bioreactor includes a first headspace airflow device and the second bioreactor includes a second headspace airflow device and each headspace airflow device operates to provide different rates of airflow across a headspace to match the operational parameter.

13. The method of claim 11, wherein the aspect ratio of the first bioprocessing container is between 1.5 and 2 and the aspect ratio of the second bioprocessing container is between 1.75 and 4.

14. The method of claim 11, wherein the first bioprocesing container is of a bench volume between 0.1 liters and 50 liters and the second bioprocessing container is of a commercial volume between 50 liters and 10,000 liters.

15. The method of claim 11, wherein the first and second bioprocessing containers are rectangular in shape and the first and second configurable mixing assemblies are offset from a center axis to achieve the operational parameter kLa.

16. The method of claim 11, wherein kLa refers to O2.

17. The method of claim 11, wherein kLa refers to CO2.

* * * * *

UNITED STATES PATENT AND TRADEMARK OFFICE
CERTIFICATE OF CORRECTION

PATENT NO. : 11,584,910 B2
APPLICATION NO. : 16/238591
DATED : February 21, 2023
INVENTOR(S) : Christopher Brau et al.

It is certified that error appears in the above-identified patent and that said Letters Patent is hereby corrected as shown below:

In the Claims

In Column 30, Line 50, Claim 1, delete "bioproces sing" and insert -- bioprocessing --, therefor.

In Column 32, Line 5, Claim 11, delete "bioproces sing" and insert -- bioprocessing --, therefor.

In Column 32, Line 9, Claim 11, delete "bioproces sing" and insert -- bioprocessing --, therefor.

In Column 32, Lines 39-40, Claim 14, delete "bioproces sing" and insert -- bioprocessing --, therefor.

In Column 32, Line 47, Claim 16, delete "O2." and insert -- $O_2$. --, therefor.

In Column 32, Line 48, Claim 17, delete "CO2." and insert -- $CO_2$. --, therefor.

Signed and Sealed this
Twenty-fifth Day of April, 2023

Katherine Kelly Vidal
*Director of the United States Patent and Trademark Office*